United States Patent
Perichon et al.

(10) Patent No.: US 10,539,575 B2
(45) Date of Patent: Jan. 21, 2020

(54) BIOMARKERS RELATED TO KIDNEY FUNCTION AND METHODS USING THE SAME

(71) Applicant: METABOLON, INC., Durham, NC (US)

(72) Inventors: Regis Perichon, Cary, NC (US); Jeffery Edmond Cobb, Chapel Hill, NC (US); Meredith V. Brown, Durham, NC (US); Adam Kennedy, Durham, NC (US)

(73) Assignee: METABOLON, INC., Morrisville, NC (US)

( * ) Notice: Subject to any disclaimer, the term of this patent is extended or adjusted under 35 U.S.C. 154(b) by 264 days.

(21) Appl. No.: 14/889,930

(22) PCT Filed: May 13, 2014

(86) PCT No.: PCT/US2014/037762
§ 371 (c)(1),
(2) Date: Nov. 9, 2015

(87) PCT Pub. No.: WO2014/186311
PCT Pub. Date: Nov. 20, 2014

(65) Prior Publication Data
US 2016/0116486 A1    Apr. 28, 2016

Related U.S. Application Data

(60) Provisional application No. 61/822,965, filed on May 14, 2013.

(51) Int. Cl.
*G01N 33/68* (2006.01)
*G01N 33/70* (2006.01)
(Continued)

(52) U.S. Cl.
CPC ..... *G01N 33/6893* (2013.01); *G01N 33/5308* (2013.01); *G01N 33/64* (2013.01);
(Continued)

(58) Field of Classification Search
CPC ............. G01N 33/5308; G01N 33/64; G01N 33/6848; G01N 33/6893; G01N 33/70;
(Continued)

(56) References Cited

U.S. PATENT DOCUMENTS 5,712,084 A    1/1998  Osgood et al.
2010/0114064 A1    5/2010  Kalafut et al.
(Continued)

FOREIGN PATENT DOCUMENTS

CN    101377492 A    1/1998
JP    H02196787 A    8/1990
(Continued)

OTHER PUBLICATIONS

Zhao et al. (Clinica Chimica Acta, 2013, 422:59-69) (Year: 2013).*
(Continued)

*Primary Examiner* — Jeremy C Flinders
(74) *Attorney, Agent, or Firm* — NK Patent Law

(57) ABSTRACT

Biomarkers of kidney function and methods for using said biomarkers for assessing kidney function, monitoring kidney function, diagnosing acute kidney injury, and diagnosing chronic kidney disease are provided. Also provided are suites of small molecule entities as biomarkers for chronic kidney disease.

17 Claims, 6 Drawing Sheets

(51) Int. Cl.
  *G01N 33/64* (2006.01)
  *G01N 33/53* (2006.01)
  *G01N 30/02* (2006.01)

(52) U.S. Cl.
  CPC ......... *G01N 33/6848* (2013.01); *G01N 33/70* (2013.01); *G01N 2570/00* (2013.01); *G01N 2800/347* (2013.01); *G01N 2800/50* (2013.01); *G01N 2800/52* (2013.01); *G01N 2800/56* (2013.01)

(58) Field of Classification Search
  CPC ......... G01N 2570/00; G01N 2800/347; G01N 2800/50; G01N 2800/52; G01N 2800/56
  See application file for complete search history.

(56) References Cited

U.S. PATENT DOCUMENTS

| | | |
|---|---|---|
| 2010/0273207 A1 | 10/2010 | Langley et al. |
| 2012/0034240 A1 | 2/2012 | Kas et al. |
| 2012/0141378 A1 | 6/2012 | Feinstein et al. |
| 2012/0193527 A1 | 8/2012 | Abe et al. |
| 2013/0115649 A1 | 5/2013 | Shuster et al. |
| 2015/0011423 A1* | 1/2015 | Kamp ............... G01N 33/6893 506/12 |

FOREIGN PATENT DOCUMENTS

| | | |
|---|---|---|
| JP | H04126099 A | 4/1992 |
| JP | 201344698 A | 3/2013 |
| JP | 2013515243 A | 5/2013 |
| JP | 2013534309 A | 9/2013 |
| JP | 2014530350 A | 11/2014 |
| WO | WO2010126146 A1 | 11/2010 |
| WO | WO2011027573 A1 | 3/2011 |
| WO | 2013/048344 | 4/2013 |
| WO | WO2013048344 A1 | 4/2013 |

OTHER PUBLICATIONS

Sun et al. (Metabolomics, 2012, 8:1181-1193) (Year: 2012).*
Toyohara et al. (Hypertension Research, 2010, 33:944-952) (Year: 2010).*
Zhang et al. (Metabolomics Research with Tandem Mass Spectrometry, Tandem Mass Spectrometry—Applications and Principles, Dr Jeevan Prasain (Ed.), ISBN: 978-953-51-0141-3, In Tech) (Year: 2012).*
Zhao et al. (Clinica Chimica Acta, 422:59-69) (Year: 2013).*
Schnackenberg et al. (Food and Chemical Toxicology, 50:3978-3983) (Year: 2012).*
Sun et al. (Metabolomics, 8:1181-1193) (Year: 2012).*
Bräunlich et al. (Exp Toxic Pathol, 49:135-139) (Year: 1997).*
PCT/US2014/037762, filed May 13, 2014, International Search Report dated Oct. 3, 2014.
PCT/US2014/037762, filed May 13, 2014, Preliminary Report on Patentability dated Nov. 17, 2015.
Gupta, et al., "The Renal Patient with Coronary Artery Disease", Journal of the American College of Cardiology, Oct. 6, 2004, vol. 44, No. 7, pp. 1343-1353.
EP 14 79 7070.1 filed May 13, 2014, Supplementary Partial European Search Report dated Dec. 5, 2016.
CN 201480027332.7, First Office Action dated Aug. 3, 2017.
JPO, Office Action for Japanese Patent Application No. 2016-514016, dated Feb. 19, 2018.
SIPO, Second Office Action for Chinese Patent Application No. 201480027332.7, dated Mar. 26, 2018.
Jianxing, Zhao, Plasma Kynurenic Acid/Tryptophan Ratio: A Sensitive and Reliable Biomarker for the Assessment of Renal Function, Renal Failure, May 7, 2013, pp. 648-653, vol. 35, No. 5, US.
Theofylaktopoulou, D., et al, A Community-Based Study on Determinants of Circulating Markers of Cellular Immune Activation and Kynurenines: the Hordaland Health Study: Determinants of Neopterin KTR and Kynurenines, Clinical and Experimental Immunology, Feb. 25, 2013, pp. 121-130, vol. 173, No. 1, GB.
Goek, Oemer-Necmi, et al., Metabolites Associate with Kidney Function Decline and Incident Chronic Kidney Disease in the General Population, Nephrology Dialysis Transplantation, Jun. 5, 2013, pp. 2131-2138, vol. 28, No. 8, GB.
EPO, European Search Report for European Patent Application No. 18183240 dated Aug. 8, 2018.
JPO, Office Action for Japanese Patent Application No. 2016-514016, dated Oct. 2, 2018.
SIPO, Third Office Action for Chinese Patent Application No. 201480027332.7, dated Nov. 13, 2018.
Wang, Xijun et al., "Urine Metabolomics Analysis for Biomarker Discovery and Detection of Jaundice Syndrome in Patients with Liver Disease", Molecular & Cellular Proteomics, Aug. 2009; pp. 370-380.
IP Australia; Examination Report for Australian Patent Application No. 2014265669 dated Jun. 21, 2019, 4 pages.
EPO; Extended European Search Report for European Patent Application No. 19176215.2 dated Jul. 22, 2019, 6 pages.
BPTO; Office Action for Brazilian Patent Application No. BR112015028253-9 dated Sep. 24, 2019, 5 pages.
IP Australia; Office Action for Australian Patent Application No. 2014265669 dated Aug. 14, 2019, 3 pages.

* cited by examiner

# BIOMARKERS RELATED TO KIDNEY FUNCTION AND METHODS USING THE SAME

CROSS-REFERENCE TO RELATED APPLICATIONS

This application is a National Stage application of International Application No. PCT/US2014/037762, filed May 13, 2014, which claims the benefit of U.S. Provisional Patent Application No. 61/822,965, filed May 14, 2013, the entire contents of which are hereby incorporated by reference.

FIELD

The invention generally relates to biomarkers for kidney function and methods based on the same biomarkers.

BACKGROUND

There is a significant unmet clinical need for a sensitive, accurate and convenient test to assess the excretory function of the kidneys (glomerular filtration rate, GFR). The most accurate measurement of renal function is the measured glomerular filtration rate (mGFR), which requires the use of ideal filtration markers (e.g., inulin, iothalamate, iohexol). Due to its complexity, this measurement is expensive, difficult to perform in routine clinical practice, and is typically only used in research studies or for potential kidney donors. Consequently, alternative measures of kidney function based on markers such as serum creatinine are used in complex equations to derive an estimated GFR (eGFR). The advantage of this approach is its ease of use in routine clinical practice for the assessment of kidney function. However, these methods of determining the GFR have limitations in truly assessing the kidney function; some equations underestimate GFR and some over-estimate GFR, especially when it is in the "normal" range. Some of these limitations are likely due to the variability of serum creatinine levels which can be affected by muscle mass, diet, and some drugs, including antibiotics, which leads to variable levels among individuals and over time. The clinical consequence of this inaccuracy leads to the misdiagnosis of patients. In some cases, individuals with chronic kidney disease (CKD) are not diagnosed by current methods and thus they do not receive appropriate treatment (false negative). In other cases, individuals may be diagnosed as having CKD when in fact they do not have CKD (false positive); these individuals are then treated for a disease they do not have. More recently serum levels of cystatin C have been used to assess kidney function, but the utility of this measure of kidney function is limited by the variability of cystatin C serum levels among individuals. Thus, there is a need for a convenient and more accurate test than the currently available kidney function assessment tests to reduce the number of false negative and false positive diagnoses.

Furthermore, current assessments of kidney function (e.g., serum creatinine, cystatin C and eGFR measurements, BUN, urine albumin) are not sufficiently sensitive and/or accurate to detect early kidney disease or to monitor its progression, especially at the earliest stages of CKD when individuals are asymptomatic. Early detection of declining kidney function could prevent significant deterioration of kidney function that may occur before the problem is detected with currently available methods. A novel test with a sensitive readout that assesses and monitors an individual's kidney function would allow for earlier detection of CKD, before CKD can be detected with current methods. As a result, the overall cost of treating and managing CKD and associated complications would be reduced. With early detection of CKD, complications, including cardiovascular disease, anemia, malnutrition and bone disease, can be more effectively treated or possibly even prevented. Early detection of CKD would enable lifestyle modifications such as healthy diet, smoking cessation, weight loss, and treatment of high blood pressure, which could prevent or reduce further kidney injury, thereby reducing the need for dialysis and kidney transplant which are frequent outcomes associated with reduced kidney function and CKD.

A blood- or urine-based test to assess and/or monitor a patient's renal function by measuring the level of one or more biomarker metabolites in patients with risk factors for CKD (e.g., age over 60, hypertension, diabetes, cardiovascular disease, family history of CKD) would be clinically useful. For example, the biomarkers could comprise a test that quantitatively measures the level of a panel of biomarker metabolites whereby the increase or decrease in the level of each biomarker in the panel relative to a standard reference level are indicative of kidney function. Such biomarker test panels could replace or supplement current kidney function test results and enable physicians to better assess kidney function initially and/or to monitor kidney function in patients over time. Such a test could also be useful in assessing the effect of therapeutic interventions to slow kidney function decline.

SUMMARY

In one aspect, the present invention provides a method of assessing or aiding in the assessment of kidney function, comprising analyzing a biological sample from a subject to determine the level(s) of one or more biomarkers for kidney function in the sample, where the one or more biomarkers are selected from the listed biomarkers: pseudouridine, N-acetylthreonine, C-glycosyltryptophan, N-acetylserine, N-acetylalanine, N6-carbamoylthreonyladenosine, 4-acetamidobutanoate, Erythritol, myo-inositol, erythronate, urea, arabitol, N2,N2-dimethylguanosine, N1-methyladenosine, 3-methylglutarylcarnitine (C6), S-adenosylhomocysteine (SAH), N-acetylmethionine, N6-acetyllysine, Kynurenine, arabonate, succinylcarnitine, ribose, xylonite, N-formylmethionine, O-methylcatechol sulfate, 2-methylbutyrylcarnitine (C5), Phenylacetylglutamine, N2,N5-diacetylornithine, creatinine, and comparing the level(s) of the one or more biomarkers in the sample to kidney function reference levels of the one or more biomarkers in order to assess the kidney function of a subject.

In another embodiment, the present invention provides a method of assessing kidney function in response to a composition, comprising analyzing a biological sample from a subject treated with a composition to determine the level(s) of one or more biomarkers for kidney function in the sample, where the one or more biomarkers are selected from the listed biomarkers: pseudouridine, N-acetylthreonine, C-glycosyltryptophan, N-acetylserine, N-acetylalanine, N6-carbamoylthreonyladenosine, 4-acetamidobutanoate, erythritol, myo-inositol, erythronate, urea, arabitol, N2,N2-dimethylguanosine, N1-methyladenosine, 3-methylglutarylcarnitine (C6), S-adenosylhomocysteine (SAH), N-acetylmethionine, N6-acetyllysine, Kynurenine, arabonate, succinylcarnitine, ribose, xylonite, N-formylmethionine, O-methylcatechol sulfate, 2-methylbutyrylcarnitine (C5), phenylacetylglutamine, N2,N5-diacetylornithine, creatinine, and comparing the level(s) of the one or more biomarkers in the sample to kidney function reference levels of the one or more biomarkers in order to assess kidney function.

In another aspect, the present invention provides a method of classifying or aiding in the classification of a subject according to level of kidney function (e.g., normal, mildly reduced, moderately reduced, severely reduced, end-stage kidney failure) comprising analyzing a biological sample from a subject to determine the level(s) of one or more biomarkers for kidney function in the sample, where the one or more biomarkers are selected from the listed biomarkers: pseudouridine, N-acetylthreonine, C-glycosyltryptophan, N-acetylserine, N-acetylalanine, N6-carbamoylthreonyladenosine, 4-acetamidobutanoate, Erythritol, myo-inositol, erythronate, urea, arabitol, N2,N2-dimethylguanosine, N1-methyladenosine, 3-methylglutarylcarnitine (C6), S-adenosylhomocysteine (SAH), N-acetylmethionine, N6-acetyllysine, Kynurenine, arabonate, succinylcarnitine, ribose, xylonite, N-formylmethionine, O-methylcatechol sulfate, 2-methylbutyrylcarnitine (C5), Phenylacetylglutamine, N2,N5-diacetylornithine, creatinine, and comparing the level(s) of the one or more biomarkers in the sample to kidney function reference levels of the one or more biomarkers in order to determine the level of kidney function of a subject.

In another embodiment, the invention provides a method of monitoring kidney function in a subject, the method comprising: analyzing a first biological sample from a subject to determine the level(s) of one or more biomarkers for kidney function, where the one or more biomarkers are selected from the listed biomarkers: pseudouridine, N-acetylthreonine, C-glycosyltryptophan, N-acetylserine, N-acetylalanine, N6-carbamoylthreonyladenosine, 4-acetamidobutanoate, Erythritol, myo-inositol, erythronate, urea, arabitol, N2,N2-dimethylguanosine, N1-methyladenosine, 3-methylglutarylcarnitine (C6), S-adenosylhomocysteine (SAH), N-acetylmethionine, N6-acetyllysine, Kynurenine, arabonate, succinylcarnitine, ribose, xylonite, N-formylmethionine, O-methylcatechol sulfate, 2-methylbutyrylcarnitine (C5), Phenylacetylglutamine, N2,N5-diacetylornithine, creatinine, and the first sample is obtained from the subject at a first time point; analyzing a second biological sample from a subject to determine the level(s) of the one or more biomarkers, where the second sample is obtained from the subject at a second time point; and comparing the level(s) of one or more biomarkers in the second sample to the level(s) of the one or more biomarkers in (a) the first sample, (b) kidney function reference levels of the one or more biomarkers, (c) CKD-positive reference levels of the one or more biomarkers, and/or (d) CKD-negative reference levels of the one or more biomarkers in order to monitor kidney function in the subject.

In a further embodiment, the invention provides a Kidney Function Score to assess kidney function and/or to monitor kidney function.

In another aspect, the present invention provides a method of diagnosing or aiding in the diagnosis of CKD, comprising analyzing a biological sample from a subject to determine the level(s) of one or more biomarkers for kidney function in the sample, where the one or more biomarkers are selected from Tables 1, 2, 3, and/or 4 and comparing the level(s) of the one or more biomarkers in the sample to CKD-positive and/or CKD-negative reference levels of the one or more biomarkers in order to determine whether the subject has CKD.

In another embodiment, the methods described herein may be used in combination with other methods (or the results thereof) useful in the assessment of kidney function in a subject. For example, clinical parameters such as BUN, SCr, and/or urine albumin measurements markers of kidney function such as β-2 microglobulin, β-TRACE, 2-mannopyranosyl tryptophan (2-MPT); as well as patient information such as, for example, family history of CKD or other risk factors can be used with the biomarkers.

In another embodiment, the methods described herein may be used to assess kidney function and/or diagnose CKD in patients with GFR estimates of 40-80 ml/min/1.73 m$^2$.

In one embodiment, a biomarker panel comprised of pseudouridine, C-glycosyltryptophan, N-acetylthreonine, and creatinine may be used to assess kidney function and/or diagnose CKD in a subject.

DETAILED DESCRIPTION

Figure 1:
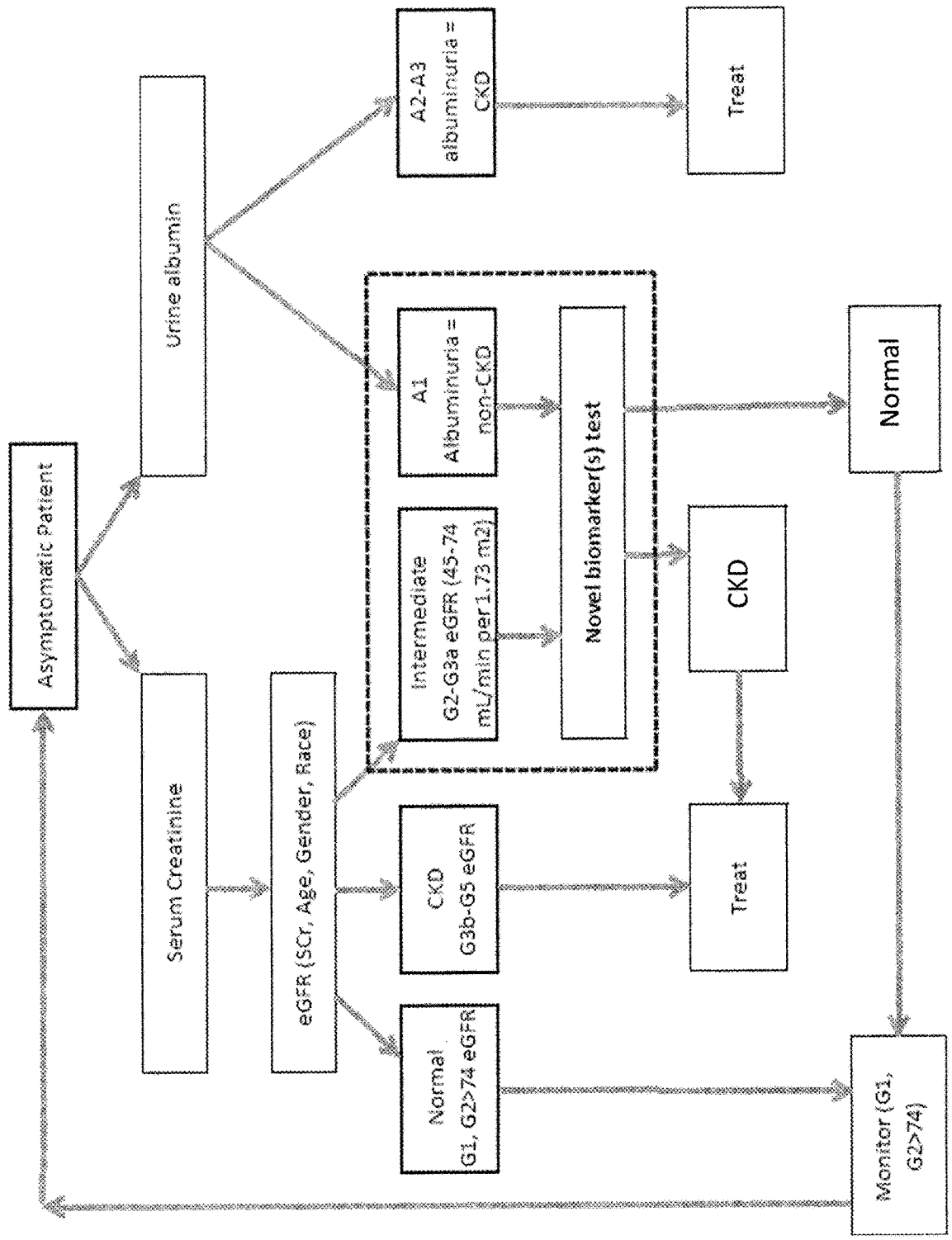
FIG. 1 is an example of an algorithm for patient management illustrating where the metabolite biomarker test (Novel biomarker(s) test) would be useful to integrate into clinical practice. Patients with eGFR and/or urine albumin scores in the range for an uncertain diagnosis (as indicated in the hashed box) would receive the metabolite biomarker test. Novel Biomarker Test refers to a Metabolite Biomarker Kidney Function Test. G1: Stage 1 CKD, GFR >90; G2: Stage 2 CKD, GFR 60-89; G3a: Stage 3 CKD, GFR 45-59; G3b: Stage 3 CKD, GFR 30-44; G4: Stage 4 CKD, GFR 15-29; G5: Stage 5 CKD, GFR <15 or on dialysis. A1: albumin-to-creatinine ratio <30 mg/g; A2: albumin-to-creatinine ratio 30-300 mg/g; A3: albumin-to-creatinine ratio >300 mg/g. CKD, chronic kidney disease; eGFR, estimated glomerular filtration rate; SCr, serum creatinine.

Biomarkers of kidney function, methods of assessing or aiding in the assessment of kidney function, methods for diagnosing or aiding in the diagnosis of chronic kidney disease (CKD); methods for classifying subjects according to level of kidney function; methods of monitoring kidney function; methods of determining susceptibility to CKD; methods of assessing kidney function in response to a composition; as well as other methods based on biomarkers of kidney function are described herein.

In one embodiment, groups (also referred to as "panels") of biomarker metabolites that can be used to assess or aid in the assessment of kidney function are identified.

Prior to describing this invention in further detail, however, the following terms will be defined.

Definitions

"Biomarker" means a compound, preferably a metabolite, that is differentially present (i.e., increased or decreased) in a biological sample from a subject or a group of subjects having a first phenotype (e.g., having a disease) as compared to a biological sample from a subject or group of subjects having a second phenotype (e.g., not having the disease). A biomarker may be differentially present at any level, but is generally present at a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (i.e., a p-value less than 0.05 and/or a q-value of less than 0.10 as determined using either Welch's T-test or Wilcoxon's rank-sum Test).

The "level" of one or more biomarkers means the absolute or relative amount or concentration of the biomarker measured in the sample.

"Sample" or "biological sample" means biological material isolated from a subject. The biological sample may contain any biological material suitable for detecting the desired biomarkers, and may comprise cellular and/or non-cellular material from the subject. The sample can be isolated from any suitable biological tissue or fluid such as, for example, kidney tissue, blood, blood plasma (plasma), blood serum (serum), urine, or cerebral spinal fluid (CSF).

"Subject" means any animal, but is preferably a mammal, such as, for example, a human, monkey, mouse, rabbit or rat.

A "reference level" of a biomarker means a level of the biomarker that is indicative of a particular disease state, phenotype, or lack thereof, as well as combinations of disease states, phenotypes, or lack thereof. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). A "positive" reference level of a biomarker means a level that is indicative of a particular disease state or phenotype. A "negative" reference level of a biomarker means a level that is indicative of a lack of a particular disease state or phenotype. For example, a "CKD-positive reference level" of a biomarker means a level of a biomarker that is indicative of a positive diagnosis of CKD in a subject, and a "CKD-negative reference level" of a biomarker means a level of a biomarker that is indicative of a negative diagnosis of CKD in a subject (i.e., normal kidney function, absence of CKD). Likewise, a "kidney function reference level" may indicate the degree of kidney function present in a subject. For example, a "normal kidney function reference level" of a biomarker means a level of a biomarker that is indicative of normal kidney function in a subject, a "moderately reduced kidney function reference level" of a biomarker means a level of a biomarker that is indicative of moderately reduced kidney function, and a "severely reduced kidney function reference level" of a biomarker means a level of a biomarker that is indicative of severely reduced kidney function in a subject.

"Non-biomarker compound" means a compound that is not differentially present in a biological sample from a subject or a group of subjects having a first phenotype (e.g., having a first disease) as compared to a biological sample from a subject or group of subjects having a second phenotype (e.g., not having the first disease). Such non-biomarker compounds may, however, be biomarkers in a biological sample from a subject or a group of subjects having a third phenotype (e.g., having a second disease) as compared to the first phenotype (e.g., having the first disease) or the second phenotype (e.g., not having the first disease).

"Metabolite", or "small molecule", means organic and inorganic molecules which are present in a cell. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates which can be metabolized further or used to generate large molecules, called macromolecules. The term "small molecules" includes signaling molecules and intermediates in the chemical reactions that transform energy derived from food into usable forms. Examples of small molecules include sugars, fatty acids, amino acids, nucleotides, intermediates formed during cellular processes, and other small molecules found within the cell.

"Glomerular filtration rate" or "GFR" is the volume of fluid filtered from the renal glomerular capillaries into the Bowman's capsule per unit time. The GFR is a metric of kidney function whereby GFR at or above a certain threshold indicates normal kidney function and GFR below the threshold value indicates kidney function is compromised or impaired. Generally, a high GFR value indicates better kidney function while a low GFR indicates kidney function impairment (e.g., chronic kidney disease, acute kidney injury).

"Estimated glomerular filtration rate" or "eGFR" means a calculated estimate of the actual glomerular filtration rate based on serum creatinine concentration. Generally, low eGFR values are associated with decreased kidney function.

"CKD-EPI eGFR" or "Chronic Kidney Disease Epidemiology Collaboration" is an equation for calculating the eGFR. The equation is: $GFR=141 \times \min(SCr/\kappa,1)^{\alpha} \times \max(SCr/\kappa,1)^{-1.209} \times 0.993^{Age} \times 1.018$ [if female]$\times 1.159$ [if black], where SCr is serum creatinine (mg/dL), $\kappa$ is 0.7 for females and 0.9 for males, $\alpha$ is $-0.329$ for females and $-0.411$ for males, min indicates the minimum of SCr/$\kappa$ or 1, and max indicates the maximum of SCr/$\kappa$ or 1.

"MDRD or "Modification of Diet in Renal Disease eGFR" is another equation for calculating the eGFR. The equation is: $eGFR=186 \times (S_{er})^{-1.154} \times (Age)^{-0.203} \times (0.742$ if female$)\times(1.212$ if Black$)$, where Scr is serum creatinine (mg/dL).

"Urine albumin" is a test measuring the amount of albumin in the urine and is also used to detect kidney disease.

"Serum creatinine" or "SCr" refers to the measurement of creatinine in serum and is commonly used to estimate GFR.

"Blood urea nitrogen" or "BUN" refers to the measurement of the amount of nitrogen in the blood in the form of urea. BUN is a test used to measure kidney function.

"Chronic Kidney Disease" or "CKD" includes conditions that damage kidneys resulting in decreased ability of the kidney to remove wastes from the body resulting in high levels of the wastes in the body and leading to increased risk of illness and development of complications such as high blood pressure, anemia, poor nutritional health and nerve damage. Patients with abnormalities in kidney function for at least three months may be diagnosed with CKD. Kidney damage due to CKD is permanent.

"Acute kidney injury" or "AKI" refers to a condition in which there is a rapid loss of kidney function. Kidney damage due to AKI may be reversible.

"Chronic Kidney Disease Stages" or "CKD Stages" means the degree of kidney damage as currently assessed using the measured or estimated glomerular filtration rate (mGFR, eGFR). Clinically, 5 stages of CKD are generally recognized with kidney function regarded as normal in Stage 1 (GFR >90), minimally reduced in Stage 2 (GFR 60-89), moderately reduced in Stages 3A and 3B (GFR 30-59), severely reduced in Stage 4 (GFR 15-29) and very severe or endstage kidney failure, also referred to as established renal failure at Stage 5 (GFR <15, or on dialysis). Kidney function stages may be used to refer to kidney damage present for any amount of time (i.e., kidney damage due to AKI or CKD).

I. Biomarkers

Generally, metabolic profiles were generated from biological samples collected from human subjects with a range of kidney function as determined by eGFR, as calculated using the CKD-EPI eGFR equation and/or the MDRD eGFR equation. Biomarkers of kidney function were identified by analyzing the levels of metabolites measured in serum and urine samples from the subjects and correlating the levels with eGFR; those molecules that correlated significantly with eGFR were selected as biomarkers of kidney function. Biomarkers of CKD, were identified by generating the metabolic profile for biological samples collected from a group of subjects having CKD (i.e., individuals with eGFR <60) and comparing said profile to the metabolic profile for biological samples from subjects not having CKD (i.e., individuals with eGFR > or =60). Those molecules differentially present, including those molecules differentially present at a level that is statistically significant (p<0.1), in the metabolic profile of serum samples from subjects with CKD as compared to the control group (e.g., subjects not diagnosed with CKD) were identified as biomarkers to diagnose CKD.

The biomarkers are discussed in more detail herein. The identified biomarkers may be used to assess kidney function in a subject, to monitor a subject to detect changes in kidney function (e.g., decreases in function which may indicate acute kidney injury or incipient CKD), to classify subjects according to the degree of kidney function (e.g., normal, mildly reduced, moderately reduced, severely reduced, end-stage kidney failure) and to distinguish subjects having CKD vs. control subjects not diagnosed with CKD (see Tables 1, 2, 3, and/or 4). Further, the biomarkers may be used to monitor changes in kidney function over time or in response to drug treatment, disease (e.g., type II diabetes), or lifestyle interventions (e.g., diet, exercise) and to identify or rule-out subjects as suitable candidates for drug therapies and/or kidney transplant.

II. Methods

A. Assessing Kidney Function Using the Biomarkers

The kidney function biomarkers can be used to assess (or aid in the assessment of) kidney function in a subject. It will be understood that the identified biomarkers can be used to assess kidney function in any subject and includes the assessment of kidney function in an asymptomatic subject, in a subject at risk of CKD or AKI due to the presence of symptoms, or risk factors (e.g., hypertension, diabetes, family history of CKD, exposure to certain chemical/environmental conditions, etc.), and in a subject in response to a composition or to a therapeutic intervention (e.g., kidney transplant, lifestyle modification). It is further understood that a subject may undergo one or more assessments of kidney function.

In an exemplary method, assessing kidney function in a subject comprises (1) analyzing a biological sample obtained from a subject to determine the level(s) of one or more biomarkers for kidney function in the sample and (2) comparing the level(s) of the one or more biomarkers in the sample to reference level(s) of the one or more biomarkers to assess kidney function in a subject and determine if kidney function is normal or impaired as well as to determine the level of kidney function impairment. The one or more biomarkers may be selected from Tables 1, 2, 3, and/or 4 and/or from the group consisting of the following biomarkers: pseudouridine, N-acetylthreonine, C-glycosyltryptophan, N-acetylserine, N-acetylalanine, N6-carbamoylthreonyladenosine, 4-acetamidobutanoate, Erythritol, myo-inositol, erythronate, urea, arabitol, N2,N2-dimethylguanosine, N1-methyladenosine, 3-methylglutarylcarnitine (C6), S-adenosylhomocysteine (SAH), N-acetylmethionine, N6-acetyllysine, Kynurenine, arabonate, succinylcarnitine, ribose, xylonite, N-formylmethionine, O-methylcatechol sulfate, 2-methylbutyrylcarnitine (C5), Phenylacetylglutamine, N2,N5-diacetylornithine, creatinine and combinations thereof. When such a method is used to aid in assessing kidney function, the results of the method may be used along with other methods (or the results thereof) and/or patient metadata useful in the clinical determination of whether a subject has normal kidney function or impaired kidney function (which can result from an acute kidney injury (AKI) or CKD as well as the level of kidney function (e.g., normal, mildly impaired, moderately impaired, severely impaired, end-stage kidney failure).

Any suitable method may be used to analyze the biological sample in order to determine the level(s) of the one or more biomarkers in the sample. Suitable methods include chromatography (e.g., HPLC, gas chromatography, liquid chromatography), mass spectrometry (e.g., MS, MS-MS), enzyme-linked immunosorbent assay (ELISA), antibody linkage, other immunochemical techniques, and combinations thereof. Further, the level(s) of the one or more biomarkers may be measured indirectly, for example, by using an assay that measures the level of a compound (or compounds) that correlates with the level of the biomarker(s) that are desired to be measured.

The level of one or more of the biomarkers selected from the listed biomarkers: pseudouridine, N-acetylthreonine, C-glycosyltryptophan, N-acetylserine, N-acetylalanine, N6-carbamoylthreonyladenosine, 4-acetamidobutanoate, Erythritol, myo-inositol, erythronate, urea, arabitol, N2,N2-dimethylguanosine, N1-methyladenosine, 3-methylglutarylcarnitine (C6), S-adenosylhomocysteine (SAH), N-acetylmethionine, N6-acetyllysine, Kynurenine, arabonate, succinylcarnitine, ribose, xylonite, N-formylmethionine, O-methylcatechol sulfate, 2-methylbutyrylcarnitine (C5), Phenylacetylglutamine, N2,N5-diacetylornithine, creatinine, may be determined in the described methods. For example, the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, etc., including a combination of all of the listed biomarkers.

Determining levels of combinations of the biomarkers may allow greater sensitivity and specificity in the described methods. For example, pair-wise analysis of two biomarkers or ratios of the levels of certain biomarkers (and non-biomarker compounds) in biological samples may allow greater sensitivity and specificity in assessing kidney function and aiding in the assessment of kidney function. For example, the ratio of myo-inositol to glycerophosphocholine (GPC), tryptophan to kynurenine, tryptophan to 3-indoxyl sulfate, and/or tryptophan to indoleacetate may be used to assess kidney function in a subject. In further examples, determining levels of combinations of two or more, three or more, four or more, and/or five or more biomarkers may allow greater sensitivity and specificity in the methods described herein. In one example, the levels of pseudouridine, C-glycnsyltryptnphan, N-acetylthrennine, and creatinine may be used to assess kidney function in a subject. In another example, the levels of pseudouridine, N-acetylthreonine, myo-inositol, and creatinine may be used to assess kidney function in a subject. In another example, the levels of N-acetylthreonine, myo-inositol, C-glycosyltryptophan, and creatinine may be used to assess kidney function in a subject. In another example, the levels of N-acetylthreonine, myo-inositol, kynurenine, and creatinine may be used to assess kidney function in a subject. In another example, the levels of pseudouridine, C-glycosyltryptophan, N-acetylthreonine, and myo-inositol may be used to assess kidney function in a subject.

The level(s) of the one or more biomarkers may be compared to kidney function reference levels using various techniques, including a simple comparison (e.g., a manual comparison). The level(s) of the one or more biomarkers in the biological sample may also be compared to reference levels using one or more statistical analyses (e.g., t-test, Welch's T-test, Wilcoxon's rank sum test, correlation analysis, Random Forest, T-score, Z-score) or using a mathematical model (e.g., algorithm, statistical model). For example, a mathematical model comprising a single algorithm or multiple algorithms may be used to assess kidney function in a subject.

The results of the method may be used along with other methods and measurements (or the results thereof) useful in the assessment of kidney function in a subject. For example, clinical parameters such as BUN, SCr, and/or urine albumin measurements; markers of kidney function such as β-2 microglobulin, β-TRACE, 2-mannopyranosyl tryptophan (2-MPT); as well as patient information such as, for example, family history of CKD or other risk factors can be used with the biomarkers.

In one example, the identification of biomarkers for kidney function allows for the assessment of (or for aiding in the assessment of) kidney function in patients undergoing imaging tests using contrast agents where the contrast imaging agents may be toxic and, as a result, may cause kidney injury. For example in a patient with reduced kidney function (e.g., Stage 2 CKD or Stage 3 or Stage 3A CKD), an accurate measure of kidney function will help patients and clinicians assess the risk to benefit ratio of imaging tests and will allow for more informed decisions.

In another example, the identification of biomarkers for kidney function allows for the assessment of (or for aiding in the assessment of) kidney function to detect incipient CKD before CKD can be diagnosed using the current standards for determining kidney function (e.g., SCr, eGFR, cystatin C urine albumin and/or BUN measurements). Clinical measures may not be sufficiently sensitive to detect early changes in kidney function or may be inaccurate in certain subjects due to, for example, chronic illness, obesity, advanced age, vegetarian diet and/or generally reduced muscle mass. For example, in a subject with type 2 diabetes, the biomarkers described herein may be used to diagnose or aid in the diagnosis of CKD. Accurate and early diagnosis of CKD may allow earlier therapeutic intervention which could delay or prevent the development of further kidney damage and more severe CKD.

In another example, an accurate assessment of kidney function in a subject who is a potential kidney donor will aid a physician in determining whether the potential donor is suitable for donating a kidney.

In another example, the biomarkers provided allow for a method of assessing kidney function in a subject being treated with a composition. The composition may be any composition, drug or therapeutic agent given to a subject to treat any disease or condition. The composition additionally may be any composition given to a patient having a disease or condition, for example, a contrast imaging agent. For example, the identification of biomarkers for kidney function also allows for assessment of the subject's response to a composition that alters kidney function as well as the assessment of the relative patient response to two or more compositions that alter kidney function. Such assessments may be used, for example, to select compositions for treating cancer for certain subjects, or to select subjects for a course of treatment or inclusion in clinical trial. Such assessments may also be used to monitor kidney function in response to a composition prior to, throughout and/or following (i.e., post-launch) the drug development process.

In another embodiment, the instant invention allows for a metabolite biomarker test to provide an accurate determination of kidney function in patients with eGFR values that are borderline normal thus enabling a clinician to select a certain treatment or modify treatment of the patients to reduce the risk of further kidney damage. Such a biomarker test overcomes limitations of current kidney function tests which do not accurately assess all patient populations, (often leading to false positive or false negative diagnoses), and do not detect early kidney function impairment (which may be indicative of AKI or incipient CKD). For example, illustrated in FIG. 1 is an example clinical practice algorithm (flow chart) that depicts best practices for screening, diagnostic evaluation, treatment, and management of clinical symptoms to diagnose CKD. Integrated into this flow chart is a kidney function biomarkers test based on analyzing the levels of a panel of biomarkers for kidney function selected from the listed biomarkers: pseudouridine, N-acetylthreonine, C-glycosyltryptophan, N-acetylserine, N-acetylalanine, N6-carbamoylthreonyladenosine, 4-acetamidobutanoate, Erythritol, myo-inositol, erythronate, urea, arabitol, N2,N2-dimethylguanosine, N1-methyladenosine, 3-methylglutarylcarnitine (C6), S-adenosylhomocysteine (SAH), N-acetylmethionine, N6-acetyllysine, Kynurenine, arabonate, succinylcarnitine, ribose, xylonite, N-formylmethionine, O-methylcatechol sulfate, 2-methylbutyrylcarnitine (C5), Phenylacetylglutamine, N2,N5-diacetylornithine, and creatinine. In this example, a patient with no symptoms of CKD may initially have kidney function assessed by measuring SCr, and eGFR and/or urine albumin as recommended by current clinical practice guidelines. CKD stages of G2-G3a as measured by eGFR and/or CKD stage A1 as measured by urine albumin often result in false positive or false negative diagnoses; confirmatory testing is recommended. Patients with these scores would receive the novel metabolite biomarker test to aid in diagnosing CKD (hashed box). Levels of kidney function biomarkers that are normal are indicative that the patient has normal kidney function. Patients diagnosed as Normal using the metabolite biomarker test would be monitored periodically to assess kidney function. A result for which the metabolite biomarkers levels at baseline are significantly above or below normal range indicate that a patient has CKD. Patients diagnosed as having CKD by using the metabolite biomarker test would receive appropriate treatment.

In one aspect, the biomarkers provided herein can be used in a mathematical or statistical model or formula to provide a physician with a numerical score ("Kidney Function Score") indicating the level of kidney function and/or the probability that a subject has compromised kidney function which may indicate AKI or CKD. The score is based upon clinically significantly changed reference level(s) for a biomarker and/or combination of biomarkers. The reference level can be derived from an algorithm or computed from indices for impaired GFR. Methods for determining a subject's Kidney Function Score may comprise comparing the level(s) of the one or more kidney function biomarkers in the sample to kidney function reference levels of the one nr more biomarkers in order to determine the subject's Kidney Function Score. The method may employ any number of markers selected from the following list: pseudouridine, N-acetylthreonine, C-glycosyltryptophan, N-acetylserine, N-acetylalanine, N6-carbamoylthreonyladenosine, 4-acetamidobutanoate, Erythritol, myo-inositol, erythronate, urea, arabitol, N2,N2-dimethylguanosine, N1-methyladenosine, 3-methylglutarylcarnitine (C6), S-adenosylhomocysteine (SAH), N-acetylmethionine, N6-acetyllysine, Kynurenine, arabonate, succinylcarnitine, ribose, xylonite, N-formylmethionine, O-methylcatechol sulfate, 2-methylbutyrylcarnitine (C5), Phenylacetylglutamine, N2,N5-diacetylornithine, and creatinine. Multiple biomarkers may be correlated with kidney function, by any method, including statistical methods such as regression analysis.

The Kidney Function Score can be used to place the subject in the range of kidney function from normal (i.e. no kidney function impairment) to mildly reduced, moderately reduced, severely reduced, or end-stage kidney failure. Non-limiting example uses of the Kidney Function Score include: assessment of kidney function; classification of kidney function; susceptibility to developing CKD; susceptibility to developing AKI; diagnosis and stage of CKD; monitoring CKD progression by periodic determination and monitoring of the Kidney Function Score; monitoring the kidney function status of kidney transplant recipients; determining a response to therapeutic intervention; evaluating drug efficacy; and determining tolerance of therapeutic and/or contrast imaging agents.

In some embodiments, the methods may be used assess kidney function over time, thereby enabling kidney function to be monitored. The change (if any) in the level(s) of the one or more biomarkers over time (i.e., in a first sample from a subject at a first time point compared to a second sample obtained from the subject at a second time point) may be indicative of altered kidney function in the patient over time. To characterize the kidney function of a subject over time, the level(s) of the one or more biomarkers in the first sample, the level(s) of the one or more biomarkers in the second sample, and/or the results of the comparison of the levels of the biomarkers in the first and second samples may be compared to reference levels of the one or more biomarkers. If the comparisons indicate that the level(s) of the one or more biomarkers are increasing or decreasing over time (e.g., in the second sample as compared to the first sample) to become more similar to the low kidney function reference levels (or less similar to the high kidney function reference levels), then the results are indicative of declining kidney function. If the comparisons indicate that the level(s) of the one or more biomarkers are increasing or decreasing over time to become more similar to the high kidney function reference levels (or less similar to the low kidney function reference levels), then the results are indicative of normal kidney function. For example, a subject may have normal kidney function at a first time point (e.g., biomarker(s) is similar to the high kidney function reference level or dissimilar to the low kidney function reference level) and remains in the normal range at a second time point (e.g., remains similar to the high kidney function reference level(s) or dissimilar to the low kidney function reference level(s)), indicating no change in kidney function. In another instance, the kidney function may be normal at a first time point (e.g., biomarker(s) is similar to the high kidney function reference level(s) or dissimilar to the low kidney function reference level(s)) then decreases at a second time point yet remains in the normal range of kidney function, indicating that although still in the normal range, the kidney function decreased. In another illustration, a subject with borderline normal kidney function at a first time point may be diagnosed with CKD based on the level(s) of the biomarker(s) at the second time point indicating a worsening of kidney function in the subject.

The difference between the relative amount of the biomarker and the reference level may also be used to assess kidney function over time. For example, if the comparisons indicate that there is a larger difference between the level(s) of the one or more biomarkers and the high kidney function reference levels (or a smaller difference between the level(s) of the one or more biomarkers and the low kidney function reference levels) over time, then the results are indicative of the patient developing declining kidney function.

After the first sample is obtained one or more additional samples may be obtained from the subject at a later point in time. In one aspect, the one or more additional samples are obtained 1, 2, 3, 4, 5, 6, or more days after the first sample. In another aspect, the one or more samples is obtained 1, 2, 3, 4, 5, 6, 7, 8, 9, 10, or more weeks after the first sample or after the initiation of treatment with the composition. In another aspect, the one or more additional samples may be obtained 1, 2, 3, 4, 5, 6, 7, 8, 9, 10, 11, 12, or more months after the first sample or after the initiation of treatment with the composition.

In another embodiment, the methods could be used to monitor kidney function in subjects having CKD or subjects suspected of being predisposed to developing CKD (e.g., at risk subjects due to family history of CKD, drug therapy, chronic illness, etc.). In one example, the biomarkers disclosed herein may be used to monitor kidney function in subjects not having CKD. For example, in a subject suspected of being predisposed to developing CKD, the biomarkers described herein may be used to monitor the development of CKD.

In another example, the biomarkers disclosed herein may be used to monitor kidney function in kidney transplant recipients.

In another embodiment, a biomarker algorithm could be used to monitor a patient's kidney function. Using the results of the biomarker algorithm in combination with current kidney function test results (e.g., SCr, eGFR, BUN, urine albumin, cystatin C) a clinician could assess the risk-benefit ratio of the drug treatment in the patient. Additionally, a biomarker algorithm could be used by clinicians treating any patient at risk for developing loss of kidney function (e.g., diabetics, hypertensive, elderly, family history, smokers, chronically ill, kidney transplant recipient, etc.). The drug therapy may be any agent used to treat any disease or condition.

Figure 2:
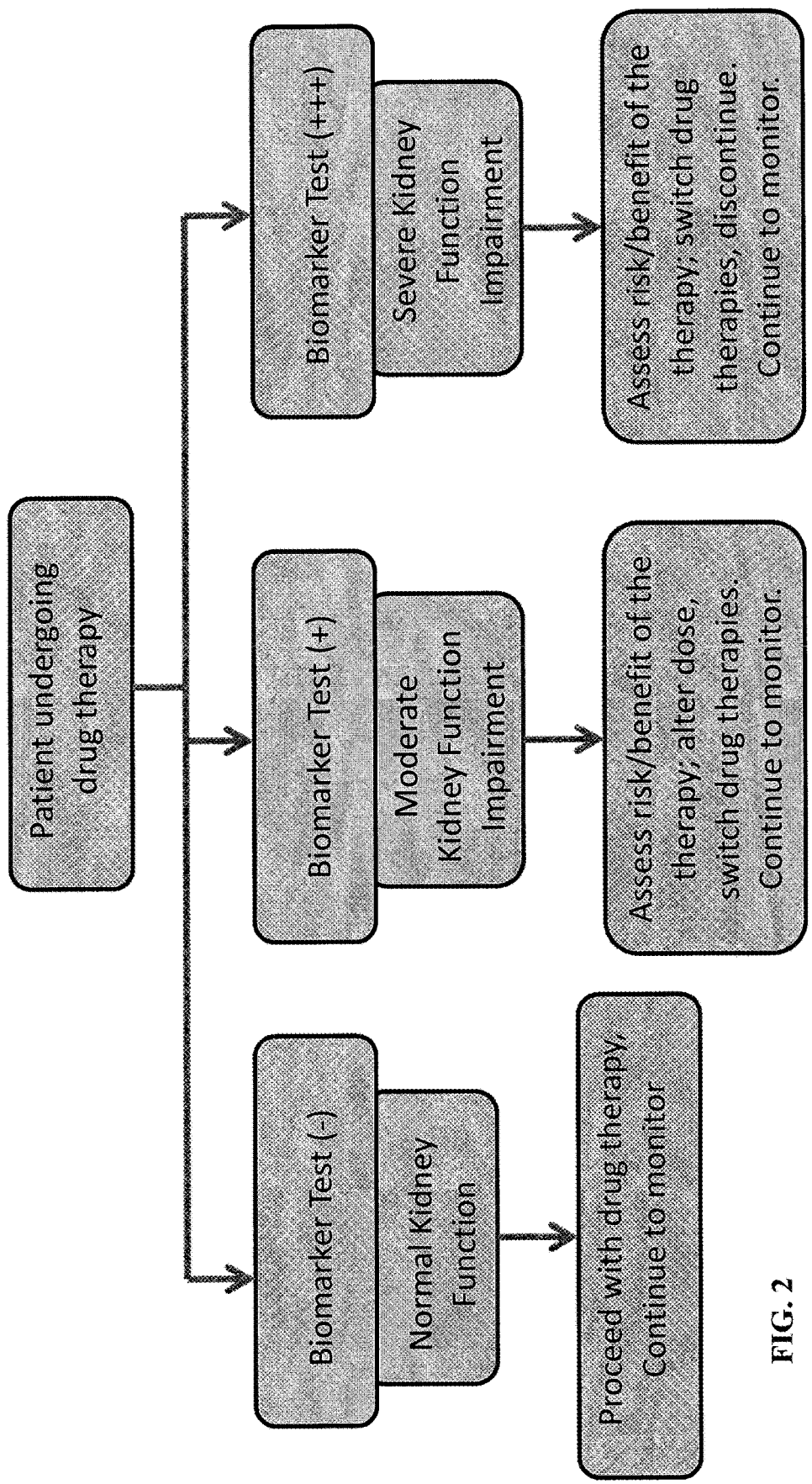
FIG. 2 is an example of an algorithm for patient management when undergoing drug therapy showing the use of the metabolite biomarker test. The level of kidney function would be assessed using the metabolite biomarker test, and recommendations for the drug therapy regimen could be made based on the results. Biomarker Test refers to Metabolite Biomarker Kidney Function Test.

Illustrated in FIG. 2 is an example of a biomarker algorithm (flow chart). Levels of kidney function biomarkers that are normal at baseline and remain within normal range during therapy, are indicative that the patient has normal kidney function.

A result for which the levels of metabolite biomarkers at baseline or the changes in these levels during therapy are outside the normal range but not excessively so would indicate that a patient has mild to moderate loss of kidney function. These patients represent those whose results would be borderline with current kidney function tests. Based on the result of the metabolite biomarker test, the treating clinician may elect to re-assess the risk-benefit of the current treatment regimen (e.g., therapeutic agent, dose) in the patient and change the patient's management.

A result for which the levels of metabolite biomarkers at baseline or the changes in these levels during therapy are significantly and excessively outside normal range would indicate that a patient has severe loss of kidney function. Changes to the patient's management would be strongly advised (e.g., discontinue treatment with particular drug, switch to another agent).

B. Diagnosing Chronic Kidney Disease Using the Biomarkers

The identification of biomarkers for kidney function also allows for the diagnosis of (or for aiding in the diagnosis of) CKD in a subject. It will be understood that the identified biomarkers can be used to diagnose or aid in diagnosing CKD in any subject, including asymptomatic subjects, those subjects presenting with one or more symptoms consistent with the presence of CKD and/or those subjects where CKD is probable (e.g., chronic illness, drug treatments, use of contrast imaging agents, etc.). In an exemplary method, diagnosing (or aiding in diagnosing) whether a subject has CKD comprises (1) analyzing a biological sample from a subject to determine the level(s) of one or more biomarkers of kidney function in the sample and (2) comparing the level(s) of the one or more biomarkers in the sample to CKD-positive and/or CKD-negative reference levels of the one or more biomarkers in order to diagnose (or aid in the diagnosis of) whether the subject has CKD. The one or more biomarkers may be selected from Table 1. When such a method is used to aid in the diagnosis of CKD, the results of the method may be used along with other methods and measurements (or the results thereof) and/or patient metadata useful in the clinical determination of whether a subject has CKD. Methods useful in the clinical determination of whether a subject has CKD are known in the art. For example, methods useful in the clinical determination of whether a subject has CKD include, for example, SCr, BUN, eGFR, mGFR, urine albumin, and cystatin C. Other measurements useful in determining whether a subject has CKD include, for example, β-2 microglobulin, β-TRACE, and/or 2-mannopyranosyl tryptophan (2-MPT). Patient metadata useful in the clinical determination of whether a subject has CKD include, for example, age, weight, gender, and race.

Any suitable method may be used to analyze the biological sample in order to determine the level(s) of the one or more biomarkers in the sample. Suitable methods include chromatography (e.g., HPLC, gas chromatography, liquid chromatography), mass spectrometry (e.g., MS, MS-MS), enzyme-linked immunosorbent assay (ELISA), antibody linkage, other immunochemical techniques, and combinations thereof. Further, the level(s) of the one or more biomarkers may be measured indirectly, for example, by using an assay that measures the level of a compound (or compounds) that correlates with the level of the biomarker(s) that are desired to be measured.

The level of one or more of the biomarkers of Table 1 may be determined in the methods of assessing and methods of aiding in the assessment of kidney function in a subject. For example, the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, etc., including a combination of any or all of the biomarkers in Table 1 or any fraction thereof, may be determined and used in such methods.

Determining levels of combinations of the biomarkers may allow greater sensitivity and specificity in diagnosing CKD and aiding in the diagnosis of CKD. For example, pair-wise analysis of two biomarkers or ratios of the levels of certain biomarkers (and non-biomarker compounds) in biological samples may allow greater sensitivity and specificity in diagnosing CKD and aiding in the diagnosis of CKD. For example, the ratio of myo-inositol to glycerophosphocholine (GPC), tryptophan to kynurenine, tryptophan to 3-indoxyl sulfate, and/or tryptophan to indoleacetate may be used to diagnose or aid in the diagnosis of CKD in a subject. In another example, determining levels of combinations of two or more, three or more, four or more, and/or five or more biomarkers may allow greater sensitivity and specificity in the methods described herein. In one example, the levels of pseudouridine, C-glycosyltryptophan, N-acetylthreonine, and creatinine may be used to diagnose or aid in the diagnosis of CKD in a subject. In another example, the levels of pseudouridine, N-acetylthreonine, myo-inositol, and creatinine may be used to diagnose or aid in the diagnosis of CKD in a subject. In another example, the levels of N-acetylthreonine, myo-inositol, C-glycosyltryptophan, and creatinine may be used to diagnose or aid in the diagnosis of CKD in a subject. In another example, the levels of N-acetylthreonine, myo-inositol, kynurenine, and creatinine may be used to diagnose or aid in the diagnosis of CKD in a subject. In another example, the levels of pseudouridine, C-glycosyltryptophan, N-acetylthreonine, and myo-inositol may be used to diagnose or aid in the diagnosis of CKD in a subject.

After the level(s) of the one or more biomarkers in the sample are determined, the level(s) are compared to CKD-positive and/or CKD-negative reference levels to diagnose or to aid in diagnosing whether the subject has CKD. Levels of the one or more biomarkers in a sample matching the CKD-positive reference levels (e.g., levels that are the same as the reference levels, substantially the same as the reference levels, slightly above and/or below the minimum and/or maximum of the reference levels, and/or within the range of the reference levels) are indicative of a diagnosis of CKD in the subject. Levels of the one or more biomarkers in a sample matching the CKD-negative reference levels (e.g., levels that are the same as the reference levels, substantially the same as the reference levels, slightly above and/or below the minimum and/or maximum of the reference levels, and/or within the range of the reference levels) are indicative of a diagnosis of no CKD in the subject. In addition, levels of the one or more biomarkers that are differentially present (especially at a level that is statistically significant) in the sample as compared to CKD-negative reference levels are indicative of a diagnosis of CKD in the subject. Levels of the one or more biomarkers that are differentially present (especially at a level that is statistically significant) in the sample as compared to CKD-positive reference levels are indicative of a diagnosis of no CKD in the subject.

The level(s) of the one or more biomarkers may be compared to CKD-positive and/or CKD-negative reference levels using various techniques, including a simple comparison (e.g., a manual comparison) of the level(s) of the one or more biomarkers in the biological sample to CKD-positive and/or CKD-negative reference levels. The level(s) of the one or more biomarkers in the biological sample may also be compared to CKD-positive and/or CKD-negative reference levels using one or more statistical analyses (e.g., t-test, Welch's T-test, Wilcoxon's rank sum test, correlation analysis, Random Forest, T-score, Z-score) or using a mathematical model (e.g., algorithm, statistical model).

For example, a mathematical model comprising a single algorithm or multiple algorithms may be used to assess kidney function in a subject. A mathematical model may also be used to determine whether a subject has CKD. A mathematical model may also be used to distinguish between CKD stages. An exemplary mathematical model may use the measured levels of any number of biomarkers (for example, 2, 3, 5, 7, 9, etc.) from a subject to determine, using an algorithm or a series of algorithms based on mathematical relationships between the levels of the measured biomarkers, whether a subject has normal kidney function or CKD, whether a subject is predisposed to developing CKD, whether CKD is progressing in a subject, whether a subject has high stage (severe or very severe kidney function reduction), mid-stage (moderately reduced function) or low stage (mildly reduced function) CKD, etc. A different exemplary mathematical model may use the measured levels of any number of biomarkers (for example, 2, 3, 5, 7, 9, etc.) from a subject to classify a subject based on the level or stage of kidney function (e.g., high, moderate, low).

In one example, the identification of biomarkers for CKD allows for the diagnosis of CKD in a subject not previously diagnosed with CKD. For example, in a subject with risk factors for CKD (e.g., age over 60 years, hypertension, diabetes, cardiovascular disease, and/or a family history of CKD, etc.), the biomarkers described herein may be used to diagnose or aid in the diagnosis of CKD.

In another example, the identification of biomarkers for CKD allows for early detection and diagnosis before CKD can be diagnosed using the current standards for determining kidney function (e.g., SCr, eGFR, urine albumin, cystatin C and/or BUN measurements). The early diagnosis of CKD may allow earlier therapeutic intervention which could delay or prevent the development of further kidney damage and more severe CKD.

In another example, the biomarkers disclosed herein may be used to diagnose or aid in diagnosing CKD in patients where the current standards for determining CKD (e.g., SCr, urine albumin, cystatin C, and/or BUN measurements) in subjects are inaccurate due to, for example, chronic illness, obesity, advanced age, vegetarian diet, and/or generally reduced muscle mass in the subject. For example, in a subject with type 2 diabetes, the biomarkers described herein may be used to diagnose or aid in the diagnosis of CKD.

C. Compositions & Kits

Any of the described methods, alone or in combination, may be performed using tools provided in the Rum of a kit. Kits may further comprise appropriate controls, standards and/or detection reagents. In an embodiment, the kit may include tools and reagents for the analysis of a blood-based sample. The kit may comprise a sample collection element and a vessel for storing the sample. For example, the kit may comprise a sample collection element, a retrieved serum collection receptacle, sample labels, sample barcodes, and instruction protocol. The instruction protocol may be provided as a printed form or booklet or on an electronic medium, such as, for example, a computer disk or other computer readable medium.

The kit may be used in accordance with the following exemplary method. A serum sample may be collected from the subject using a needle and syringe. The serum can then be extruded into a collection receptacle (e.g., a vial, a conical tube, etc.). The sample in the collection receptacle may then be subjected to biochemical analysis. Barcodes and labels enable the sample identity and the analyses results to be tracked through the biochemical analysis.

The invention will be further explained with the following examples which are offered by illustration and not limitation.

EXAMPLES

I. General Methods

A. Identification of Metabolic Profiles

Generally, each sample was analyzed to determine the concentration of several hundred metabolites. Analytical techniques such as GC-MS (gas chromatography-mass spectrometry) and LC-MS (liquid chromatography-mass spectrometry) were used to analyze the metabolites. Multiple aliquots were simultaneously, and in parallel, analyzed, and, after appropriate quality control (QC), the information derived from each analysis was recombined. Every sample was characterized according to several thousand characteristics, which ultimately amount to several hundred chemical species. The techniques used were able to identify novel and chemically unnamed compounds.

Samples were collected from a cohort of patients as described in Example 1. Metabolites were extracted and proteins were precipitated from the samples (100 µl) by the addition of 450 µl of methanol. Two separate UPLC methods were utilized, one in acidic conditions and the other in basic conditions. The precipitated extract was split into four aliquots and dried under nitrogen and then in vacuo. One aliquot was reconstituted in 50 µl of 0.1% formic acid in water (for use in the acidic method), and another aliquot was reconstituted in 50 µl of 6.5 mM ammonium bicarbonate in water, pH 8 (for use in the basic method).

Both methods used chromatography which was performed on 2.1 mm×100 mm Acquity 1.7 um C18 BEH columns (Waters Corp., Milford, Mass., USA) using an Acquity UPLC system. The mobile phase, at a flow rate of 350 µL/min, used solvent A, 0.1% formic acid in water, and solvent B, 0.1% formic acid in methanol (gradient profile: 0% B to 70% B in 4 min, 70 to 98% B in 0.5 min, 98% B for 0.9 min), for the acidic method. Sample aliquots processed for the basic method were gradient-eluted at a flow rate of 350 µL/min using solvent A, 6.5 mM ammonium bicarbonate in water, pH 8, and solvent B, 6.5 mM ammonium bicarbonate in 95/5 methanol/water (gradient profile: 0% B to 70% B in 4 min, 70 to 98% B in 0.5 min, 98% B for 0.9 min).

The sample eluents were analyzed using an LTQ mass spectrometer (MS) (ThermoFisher Corporation) using electrospray ionization (ESI). The acidic method monitored for positive ions and the basic method monitored for negative ions in independent injections using separate acid/base dedicated columns heated to 40° C. The MS interface capillary was maintained at 350° C., with a sheath gas flow of 40 (arbitrary units) and aux gas flow of 5 (arbitrary units) for both positive and negative injections. The spray voltage for the positive ion injection was 4.5 kV and 3.75 kV for the negative ion injection. The instrument scanned 99-1000 m/z and alternated between MS and MS/MS scans. The scan speed was approximately 6 scans/sec (3 MS and 3 MS/MS scans). MS/MS normalized collision energy was set to 40, activation Q 0.25, and activation time 30 ms, with a 3 m/z isolation window. MS/MS scans were collected using dynamic exclusion with an exclusion time of 3.5 sec. Isotopically labeled compounds were spiked into every sample and were used to assess instrument performance and suitability, including retention time, mass and sensitivity stability over the course of the run (usually 20 hours). In addition, a quality control sample, which consisted of a pooled aliquot from all samples, was analyzed every 8 injections to ensure technical reproducibility.

Software using standard industry approaches for MS peak detection was used for the detection and integration of MS peaks. Briefly, extracted ion chromatograms were binned by mass in a given range, baseline noise was determined, peak areas were calculated, and various user-defined peak thresholds including minimum height, signal-to-noise, width, symmetry, and area were applied to detected MS peaks. MS peaks passing above threshold criteria were assembled into lists that were then inserted into a relational database for storage and further analysis. Finally, individual MS peaks were grouped based on peak apex retention time for ease of viewing similarly retained ion features. All samples were aligned based on retention time (RT) markers present throughout the chromatogram using a retention index (RI). The retention index of a sample component is a number, obtained by interpolation (usually logarithmic), relating the adjusted retention volume (time) or the retention factor of the sample component to the adjusted retention volumes (times) of two standards eluted before and after the peak of the sample component.

The resulting data were searched against a chemical library generated specifically for each method (e.g. UPLC positive ion data was searched against a library specific for UPLC positive ion mode). Biochemical identifications were based on three criteria: retention index within 75 RI units of the proposed identification (or approximately 5 s), experimental precursor mass match to the library within 0.4 m/z, and the MS/MS forward and reverse scores. The MS/MS scores were based on a comparison of the ions present in the experimental spectrum to the ions present in the library spectrum. Biochemical identification was performed by a software program, and the computer generated identification was verified by a human analyst.

Computer software checked all ions that were not assigned to any library entry across a set of injections and within a specified chromatographic time window. By correlating ions across multiple injections, the natural biological variability of biochemicals was used to identify possible new authentic biochemicals that were not already included as an entry as part of the library. Any biochemicals that did not have a library match but were determined to be bona fide biochemicals based on the recurrent nature of the spectral pattern for that biochemical were added to the library so that the biochemical, although unnamed, could be tracked in current and future studies. Thus, although the biochemical was not identified (because an authentic chemical standard was not available in the library), the properties or behavior of the biochemical that were obtained from the analysis method were indicated, without indicating the specific chemical composition or structure of the biochemical (referred to as unnamed biochemicals).

Unnamed biochemicals represent entities for which the "ion fragmentation signature" has been established but for which no known standard is available in the chemical library. The unnamed biochemicals have been sufficiently characterized by analytical techniques (described above) for unique identification. The unnamed biochemicals are designated herein by the nomenclature "X-" followed by a specific five digit number. Identifying analytical information for the unnamed biochemical small molecules listed in Table 1 is described. For example, for unnamed metabolite X-17299, the retention time was 1.2, the retention index was 1265.9, the quant mass was 229.2, and the polarity of the quantitative ion using the analytical methods described above was positive as measured on the LC-MS/MS optimized for acidic species. In an additional example, for unnamed metabolite X-11564, the retention time was 1.2, the retention index was 1188, the quant mass was 177.1, and the polarity of the quantitative ion using the analytical methods described above was negative as measured on the LC-MS/MS optimized for basic species. These analytical characteristics allow said biomarkers (X-17299 and X-11564) to be monitored even though an exact chemical identity (i.e., compound name) is not known.

B. Statistical Analysis

The data were analyzed using t-tests to identify molecules (either known, named metabolites or unnamed metabolites) present at differential levels in a definable population or subpopulation (e.g., biomarkers for subjects with kidney function impairment compared to subjects without kidney function impairment) useful for distinguishing between the definable populations (e.g., kidney function impairment and no kidney function impairment). Other molecules (either known, named metabolites or unnamed metabolites) in the definable population or subpopulation were also identified.

The data were also analyzed using correlation analysis to identify molecules (either known, named metabolites or unnamed metabolites) that correlate with eGFR calculations (e.g., CKD-EPI eGFR, MDRD eGFR).

Multiple regression analysis was used to evaluate the predictive value for exemplary panels of biomarkers.

Based on the metabolite biomarker level, the sensitivity and specificity for the classification of the samples were calculated. Sensitivity is the ability to identify positives or the proportion of subjects classified as positive among all those that are truly positive. Specificity is the ability to identify, negatives or the proportion of the subjects classified as negative among all those that are truly negative. Using these data, a receiver operating characteristic (ROC) curve was generated. The ROC curve is a mathematical model and is a plot of the sensitivity vs. false positive rate (1 specificity). The area under the curve (AUC) from this curve is the probability that a classifier will rank a randomly chosen positive instance higher than a randomly chosen negative one.

Example 1: Biomarkers to Assess Kidney Function

The samples used for the analysis were serum samples collected from 281 diabetic individuals. Patient kidney function was evaluated using two equations for estimating GFR, 1) MDRD eGFR and 2) CKD-EPI eGFR. Using the MDRD eGFR estimates, patients with eGFR less than 60 ml/min/1.73 $m^2$ were classified as having CKD, and the patients with eGFR=60 ml/min/1.73 $m^2$ or greater were classified as Normal. A total of 46 patients were classified as having CKD, and 235 patients were classified as Normal at the time of sample collection.

After the levels of metabolites were determined, the data were analyzed using t-tests. Biomarkers for kidney function were identified by comparing CKD vs. Normal samples. As listed in Table 1 below, the analysis resulted in the identification of biomarkers that are differentially present between CKD and Normal patient serum samples. All biomarkers in Table 1 are statistically significant ($p<0.1$). As another way to identify biomarkers for kidney function impairment, a correlation analysis was performed between biomarker levels and eGFR calculations (i.e., MDRD eGFR and CKD-EPI eGFR). The correlation value for each biomarker is shown in Table 1.

Table 1 includes, for each biomarker, the biochemical name of the biomarker, the correlation value of the biomarker with MDRD, the correlation value of the biomarker with CKD-EPI, the fold change of the biomarker in subjects with CKD compared to Normal subjects (CKD/Normal) which is the ratio of the mean level of the biomarker in CKD samples as compared to the Normal mean level, and the p-value determined in the statistical analysis of the data concerning the biomarkers. Table 1 also lists the following: the identifier for the biomarker compound in the Kyoto Encyclopedia of Genes and Genomes (KEGG), if available; and the identifier for the biomarker compound in the Human Metabolome Database (HMDB), if available.

TABLE 1

Biomarkers to assess kidney function

| Biochemical Name | Correlation with eGFR by: | | Fold Change | CKD/Normal | | |
| --- | --- | --- | --- | --- | --- | --- |
| | MDRD | CKD-EPI | | P-value | KEGG | HMDB |
| N-acetylthreonine | −0.6187 | −0.6897 | 1.5403 | p < 0.0001 | C01118 | |
| erythronate | −0.5298 | −0.6393 | 1.5487 | p < 0.0001 | | HMDB00613 |
| N-acetylalanine | −0.5848 | −0.6502 | 1.3258 | p < 0.0001 | C02847 | HMDB00766 |
| arabitol | −0.5153 | −0.6022 | 2.0099 | p < 0.0001 | C00474 | HMDB01851 |
| N-acetylserine | −0.6004 | −0.6736 | 1.6718 | p < 0.0001 | | HMDB02931 |
| myo-inositol | −0.544 | −0.6216 | 1.7167 | p < 0.0001 | C00137 | HMDB00211 |
| kynurenine | −0.4968 | −0.5619 | 1.3355 | p < 0.0001 | C00328 | HMDB00684 |
| trans-4-hydroxyproline | −0.1227 | −0.1345 | 1.1241 | 0.135235 | C01157 | HMDB00725 |
| tryptophan | 0.2418 | 0.2986 | 0.8968 | 0.0002 | C00078 | HMDB00929 |

TABLE 1-continued

Biomarkers to assess kidney function

| Biochemical Name | Correlation with eGFR by: MDRD | Correlation with eGFR by: CKD-EPI | Fold Change | CKD/Normal P-value | KEGG | HMDB |
|---|---|---|---|---|---|---|
| 3-methylhistidine | −0.224 | −0.2979 | 1.8903 | 0.0017 | C01152 | HMDB00479 |
| 4-acetamidobutanoate | −0.5563 | −0.6526 | 1.5779 | p < 0.0001 | C02946 | HMDB03681 |
| N6-carbamoylthreonyladenosine | −0.584 | −0.6704 | 1.6955 | p < 0.0001 | | |
| erythritol | −0.5563 | −0.6362 | 1.9232 | p < 0.0001 | C00503 | HMDB02994 |
| 3-methylglutarylcarnitine (C6) | −0.5013 | −0.5784 | 2.5612 | p < 0.0001 | | HMDB00552 |
| S-adenosylhomocysteine (SAH) | −0.501 | −0.5799 | 1.5955 | p < 0.0001 | C00021 | HMDB00939 |
| N1-methyladenosine | −0.502 | −0.5713 | 1.2493 | p < 0.0001 | C02494 | HMDB03331 |
| N2,N2-dimethylguanosine | −0.5047 | −0.5656 | 1.4345 | p < 0.0001 | | HMDB04824 |
| N-acetylcarnosine | −0.4513 | −0.4846 | 1.5465 | p < 0.0001 | | |
| arabonate | −0.4849 | −0.562 | 1.949 | p < 0.0001 | | HMDB00539 |
| p-cresol sulfate | −0.3864 | −0.4835 | 1.92 | p < 0.0001 | C01468 | HMDB11635 |
| xylonate | −0.461 | −0.5561 | 1.775 | p < 0.0001 | C05411 | |
| N-formylmethionine | −0.4554 | −0.5439 | 1.382 | p < 0.0001 | C03145 | HMDB01015 |
| succinylcarnitine | −0.4716 | −0.5435 | 1.6696 | p < 0.0001 | | |
| O-methylcatechol sulfate | −0.4525 | −0.5431 | 2.1496 | p < 0.0001 | | |
| N-acetylmethionine | −0.5005 | −0.5381 | 1.5394 | p < 0.0001 | C02712 | HMDB11745 |
| N2,N5-diacetylornithine | −0.4462 | −0.5328 | 1.9997 | p < 0.0001 | | |
| ribose | −0.4688 | −0.5324 | 2.1962 | p < 0.0001 | C00121 | HMDB00283 |
| 2-methylbutyrylcarnitine (C5) | −0.4514 | −0.5212 | 1.7446 | p < 0.0001 | | HMDB00378 |
| N4-acetylcytidine | −0.4512 | −0.4937 | 1.5599 | p < 0.0001 | | HMDB05923 |
| N1-Methyl-2-byridone-5-carboxamide | −0.4459 | −0.4919 | 1.6845 | p < 0.0001 | C05842 | HMDB04193 |
| 1-methylhistidine | −0.423 | −0.4809 | 2.1189 | 0.0006 | C01152 | HMDB00001 |
| pyroglutamine | −0.4327 | −0.4782 | 1.629 | p < 0.0001 | | |
| tiglyl carnitine | −0.4342 | −0.4762 | 1.483 | 0.0001 | | HMDB02366 |
| 5-methylthioadenosine MTA | −0.3689 | −0.4654 | 1.7931 | p < 0.0001 | C00170 | HMDB01173 |
| isobutyrylcarnitine | −0.3896 | −0.4634 | 1.9746 | p < 0.0001 | | HMDB00736 |
| indolelactate | −0.3987 | −0.4565 | 1.434 | 0.0002 | C02043 | HMDB00671 |
| glutarylcarnitine (C5) | −0.4069 | −0.447 | 1.4393 | p < 0.0001 | | HMDB13130 |
| choline | −0.3417 | −0.4423 | 1.2088 | p < 0.0001 | C00114 | |
| 1-methylurate | −0.3759 | −0.4346 | 1.5167 | p < 0.0001 | | HMDB03099 |
| hydroxyisoyaleroyl carnitine | −0.3817 | −0.4264 | 1.668 | p < 0.0001 | | |
| pro-hydroxy-pro | −0.376 | −0.4263 | 1.7757 | 0.0006 | | HMDB06695 |
| N-acetyl-3-methylhistidine | −0.3329 | −0.4102 | 1.7492 | 0.0067 | | |
| salicyluric glucuronide | −0.3123 | −0.4062 | 4.578 | 0.0036 | | |
| scyllo-inositol | −0.3506 | −0.3965 | 1.5525 | 0.0013 | C06153 | HMDB06088 |
| quinate | −0.3438 | −0.3928 | 1.922 | 0.0021 | C00296 | HMDB03072 |
| 2,3-dihydroxyisovalerate | −0.3285 | −0.375 | 2.5621 | 0.0036 | C04039 | |
| trigonelline (NF'-methylnicotinate) | −0.3246 | −0.3691 | 1.7038 | p < 0.0001 | C01004 | HMDB00875 |
| propionylcarnitine | −0.3266 | −0.3629 | 1.3841 | 0.0001 | C03017 | HMDB00824 |
| 3-methylxanthine | −0.3153 | −0.3558 | 1.66 | 0.0051 | C16357 | HMDB01886 |
| 1,3,7-trimethylurate | −0.3243 | −0.3426 | 1.901 | 0.0041 | C16361 | HMDB02123 |
| tartarate | −0.2925 | −0.3371 | 2.7353 | 0.0088 | C00898 | HMDB00956 |
| phenylcarnitine | −0.2847 | −0.3328 | 2.1264 | 0.0358 | | |
| N-acetylphenylalanine | −0.2945 | −0.3318 | 1.381 | 0.0002 | C03519 | HMDB00512 |
| 3-methyl catechol sulfate 1 | −0.3161 | −0.3304 | 1.7389 | 0.0018 | | |
| 4-hydroxyphenylacetate | −0.264 | −0.3282 | 1.816 | 0.0306 | C00642 | HMDB00020 |
| cystine | −0.2673 | −0.3209 | 1.9586 | 0.0245 | C00491 | HMDB00192 |
| acetylcarnitine | −0.2831 | −0.3159 | 1.1845 | 0.0014 | CO2571 | HMDB00201 |
| guanosine | −0.2982 | −0.3139 | 1.537 | p < 0.0001 | C00387 | HMDB00133 |
| furosemide | −0.2481 | −0.3057 | 2.0624 | 0.0185 | D00331 | HMDB01933 |
| xanthine | −0.2493 | −0.2949 | 1.9277 | 0.0425 | C00385 | HMDB00292 |
| 4-acetylphenol sulfate | −0.297 | −0.285 | 1.9232 | 0.0012 | C00548 | |
| cis-4-decenoyl carnitine | −0.2656 | −0.2831 | 1.3248 | 0.0028 | | |
| phenyllactate (PLA) | −0.2415 | −0.2804 | 1.5813 | 0.0447 | C05607 | HMDB00779 |
| stachydrine | −0.219 | −0.2628 | 1.6889 | 0.0059 | C10172 | HMDB04827 |
| N-delta-acetylornithine | −0.1927 | −0.2494 | 1.7173 | 0.0004 | | |
| 5-acetylamino-6-formylamino-3-methyluracil | −0.2297 | −0.2439 | 2.4545 | 0.0179 | C16365 | HMDB11105 |
| 2-aminophenol sulfate | −0.2355 | −0.2414 | 1.6228 | 0.0005 | | |
| chiro-inositol | −0.1817 | −0.2405 | 2.2202 | 0.0266 | | |
| mannitol | −0.1836 | −0.2397 | 3.0328 | 0.018 | C00392 | HMDB00765 |
| taurocholenate sulfate | −0.199 | −0.2297 | 1.9086 | 0.014 | | |
| hydrochlorothiazide | −0.1787 | −0.2196 | 2.1933 | 0.0336 | C07041 | HMDB01928 |
| 1-linoleoylglycerol (1-monolinolein) | −0.1768 | −0.1966 | 1.5333 | 0.0016 | | |
| histidylphenylalanine | −0.0172 | −0.0069 | 0.3352 | 0.0317 | | |

TABLE 1-continued

Biomarkers to assess kidney function

| Biochemical Name | Correlation with eGFR by: MDRD | Correlation with eGFR by: CKD-EPI | Fold Change | CKD/Normal P-value | KEGG | HMDB |
|---|---|---|---|---|---|---|
| ADSGEGDFXAEGGGVR | 0.0259 | 0.0269 | 0.3517 | 0.0181 | | |
| HXGXA | 0.0716 | 0.1187 | 0.3912 | 0.002 | | |
| stearoyl sphingomyelin | 0.123 | 0.1254 | 0.8587 | 0.002 | C00550 | HMDB01348 |
| 3-methyl-2-oxovalerate | 0.1222 | 0.142 | 0.9061 | 0.0553776 | C00671 | HMDB03736 |
| oleamide | 0.2356 | 0.1621 | 0.1499 | $p < 0.0001$ | | HMDB02117 |
| 4-methyl-2-oxopentanoate | 0.1603 | 0.1732 | 0.9022 | 0.0474 | C00233 | HMDB00695 |
| 3-methyl-2-oxobutyrate | 0.1499 | 0.1955 | 0.9085 | 0.0087 | C00141 | HMDB00019 |
| lathosterol | 0.1904 | 0.2377 | 0.7393 | 0.0024 | C01189 | HMDB01170 |
| glycerophosphorylcholine (GPC) | 0.3754 | 0.3384 | 0.6102 | $p < 0.0001$ | C00670 | HMDB00086 |
| indoleacetylglutamine | −0.183 | −0.22 | 1.6285 | 0.0023 | | |
| palmitoyl sphingomyelin | 0.1465 | 0.1794 | 0.8685 | 0.0001 | | |
| urea | −0.5269 | −0.5702 | 1.4498 | $p < 0.0001$ | C00086 | HMDB00294 |
| X-11564 | −0.6573 | −0.5961 | 1.0487 | 0.390639 | | |
| X-17299 | −0.6484 | −0.582 | 1.1898 | 0.012403 | | |
| pseudouridine | −0.6659 | −0.7484 | 1.6032 | $p < 0.0001$ | C02067 | HMDB00767 |
| C-glycosyltryptophan | −0.6017 | −0.6928 | 1.6913 | $p < 0.0001$ | | |
| creatinine | −0.6322 | −0.6732 | 1.4077 | $p < 0.0001$ | C00791 | HMDB00562 |
| N6-acetyllysine | −0.4973 | −0.5513 | 1.368 | $p < 0.0001$ | C02727 | HMDB00206 |
| phenylacetylglutamine | −0.4481 | −0.5484 | 2.2309 | $p < 0.0001$ | C04148 | HMDB06344 |
| threitol | −0.4189 | −0.4883 | 1.9801 | $p < 0.0001$ | C16884 | HMDB04136 |
| 3-indoxyl sulfate | −0.3875 | −0.4422 | 1.4877 | $p < 0.0001$ | | HMDB00682 |
| 2-hydroxyhippurate (salicylurate) | −0.1561 | −0.2047 | 5.3527 | 0.0145 | C07588 | HMDB00840 |

Example 2: Diagnostic Performance of Individual Biomarkers for Kidney Function Assessment In another example, three exemplary biomarkers to assess kidney function and identify individuals with CKD were selected from Table 1 and evaluated for diagnostic performance. These models are intended to be non-limiting and are presented to exemplify the invention. The biomarkers identified were present at levels that differed between patient samples from individuals with normal kidney function and samples from individuals with CKD. For example, C-glycosyltryptophan, N-acetylthreonine, and pesudouridine were significant biomarkers for distinguishing subjects with CKD from normal subjects.

The samples used for the analysis were serum samples collected from 281 diabetic individuals. Patient kidney function was evaluated using the MDRD equation to estimate GFR. Patients with MDRD eGFR values of less than 60 ml/min/1.73 m² were classified as having CKD, and patients with eGFR values of 60 ml/min/1.73 m² or greater were classified as Normal. A total of 46 patients were classified as having CKD, and 235 patients were classified as Normal at the time of sample collection. The biomarkers identified in Example 1, Table 1, for diagnosing or aiding in the diagnosis of CKD were evaluated for diagnostic performance using Receiver Operator Characteristic (ROC) curve modeling.

Figure 3B:
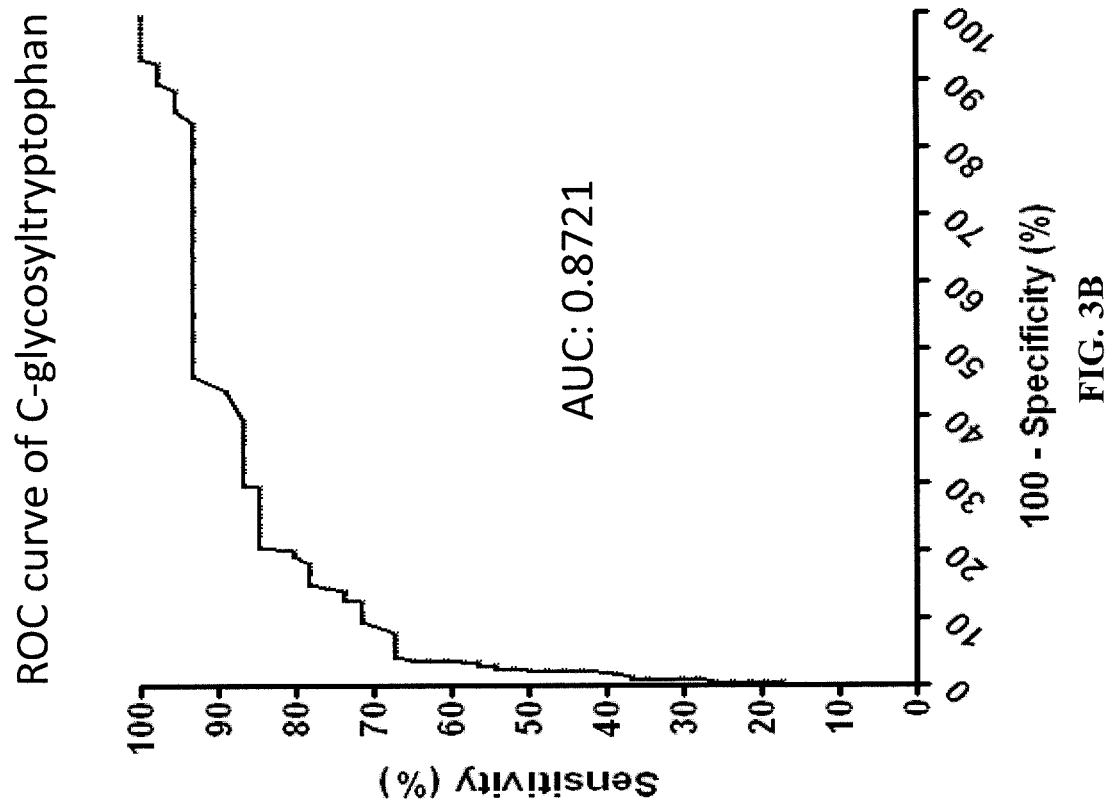
FIG. 3B is a graphical illustration of a ROC curve generated using the exemplary biomarker C-glycosyltryptophan to distinguish CKD from Normal as described in Example 2.
Figure 3A:
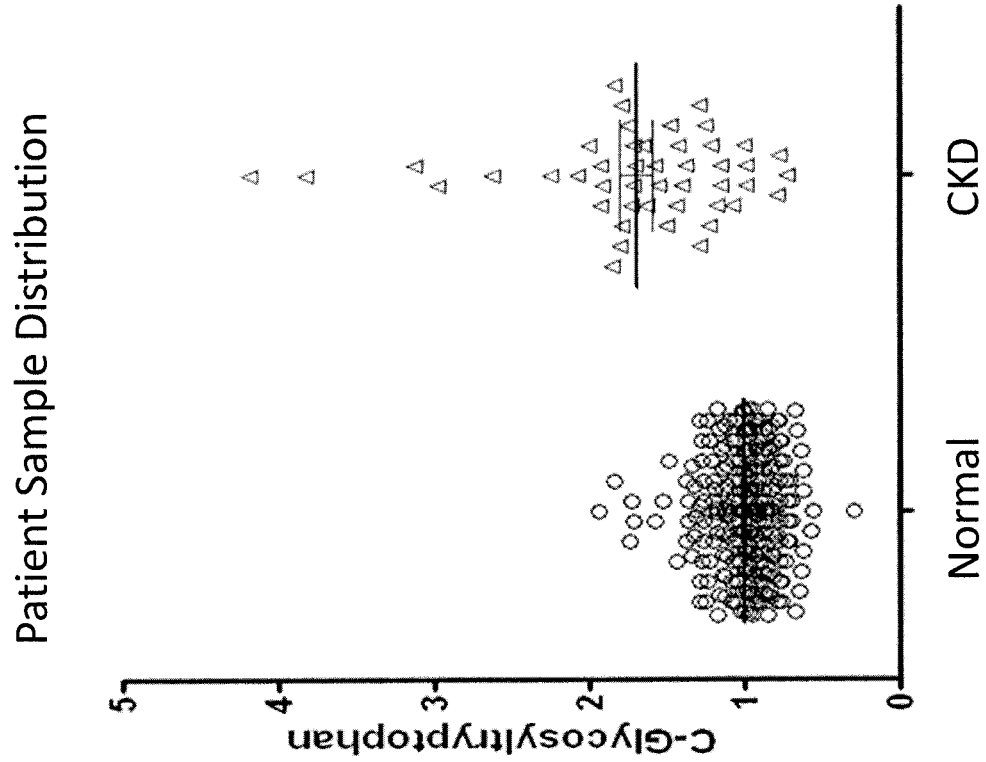
FIG. 3A is a graphical illustration of the distribution of patient serum samples based on the level of C-glycosyltryptophan measured in the sample as described in Example 2.

The exemplary biomarker C-glycosyltryptophan was evaluated for diagnostic performance. FIG. 3A shows the distribution of patient samples based on the level of C-glycosyltryptophan measured in the samples. The x-axis shows the diagnosis group (Normal or CKD), and the y-axis shows the level of C-glycosyltryptophan. Next, the levels of C-glycosyltryptophan were used in a mathematical model to determine the diagnostic performance of the biomarker. FIG. 3B shows the ROC curve for C-glycosyltryptophan. The ROC curve has an area under the curve (AUC) of 0.8721. Based on this ROC curve, it was determined that by measuring the level of C-glycosyltryptophan, CKD subjects were distinguished from Normal subjects with 85% sensitivity and 80% specificity.

Figure 4A:
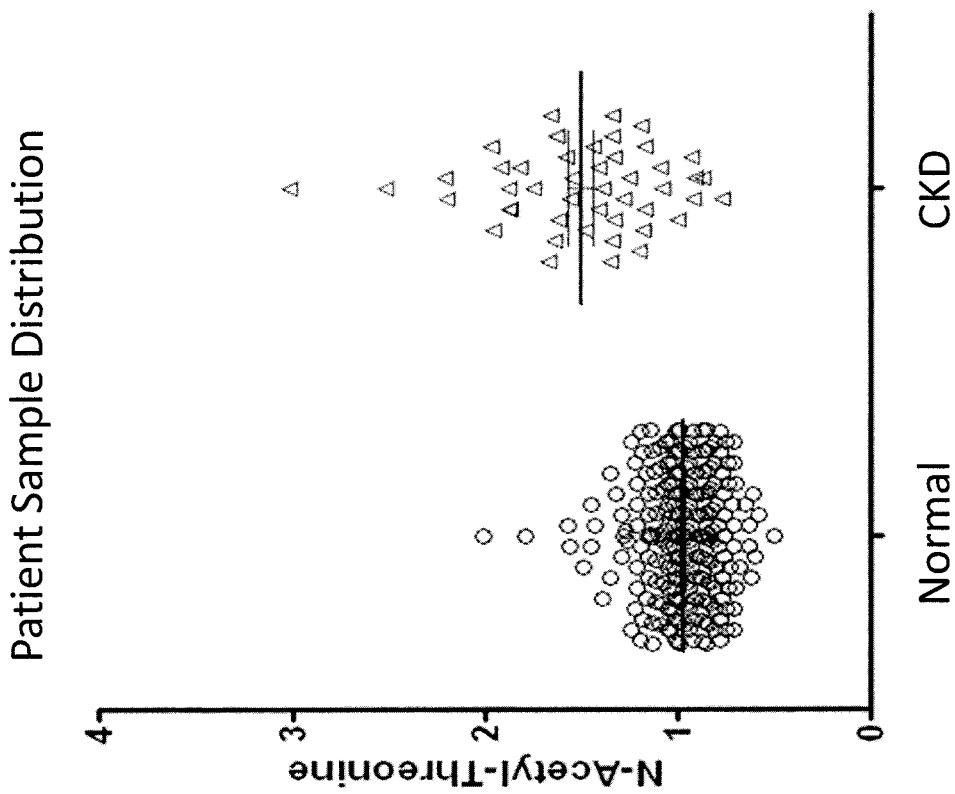
FIG. 4A is a graphical illustration of the distribution of patient serum samples based on the level of N-acetylthreonine measured in the sample as described in Example 2.
Figure 4B:
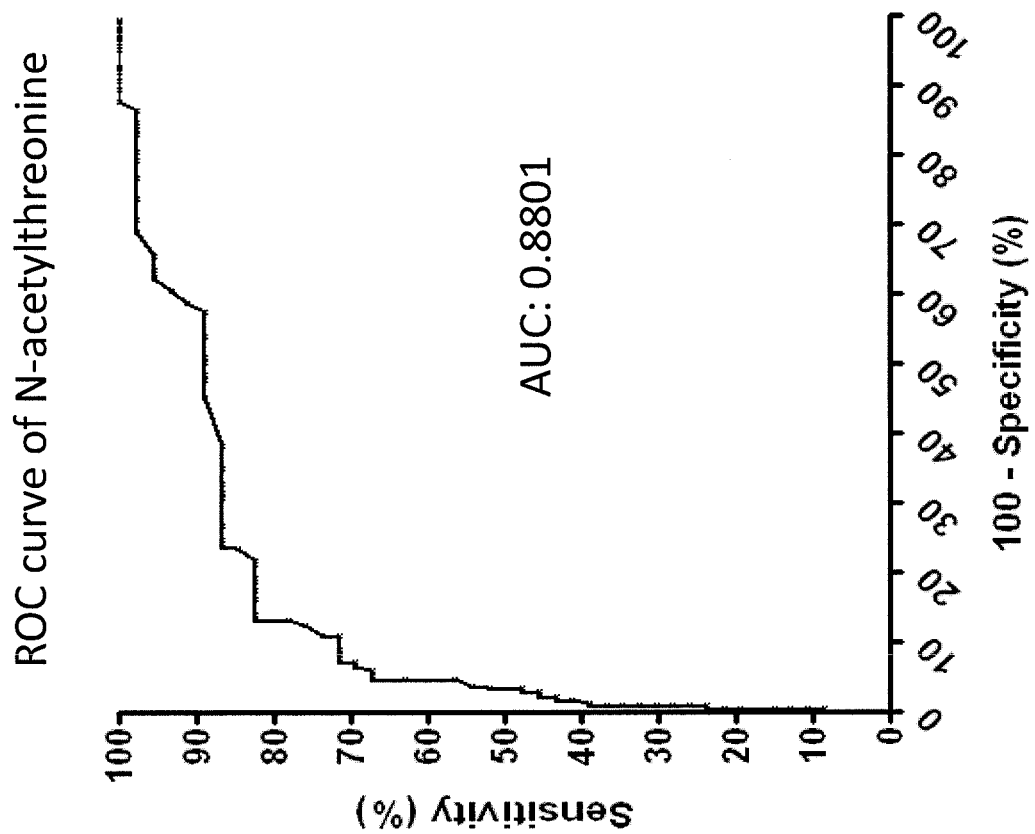
FIG. 4B is a graphical illustration of a ROC curve generated using the exemplary biomarker N-acetylthreonine to distinguish CKD from Normal as described in Example 2.

The exemplary biomarker N-acetylthreonine was also evaluated for diagnostic performance. FIG. 4A shows the distribution of patient samples based on the level of N-acetylthreonine measured in the samples. The x-axis shows the diagnosis group (Normal or CKD), and the y-axis shows the level of N-acetylthreonine. Next, the levels of N-acetylthreonine were used in a mathematical model to determine the diagnostic performance of the biomarker. FIG. 4B shows the ROC curve for N-acetylthreonine. The ROC curve has an AUC of 0.8801. Based on this ROC curve it was determined that by measuring the level of N-acetylthreonine, CKD subjects were distinguished from normal subjects with 83% sensitivity and 87% specificity.

Figure 5B:
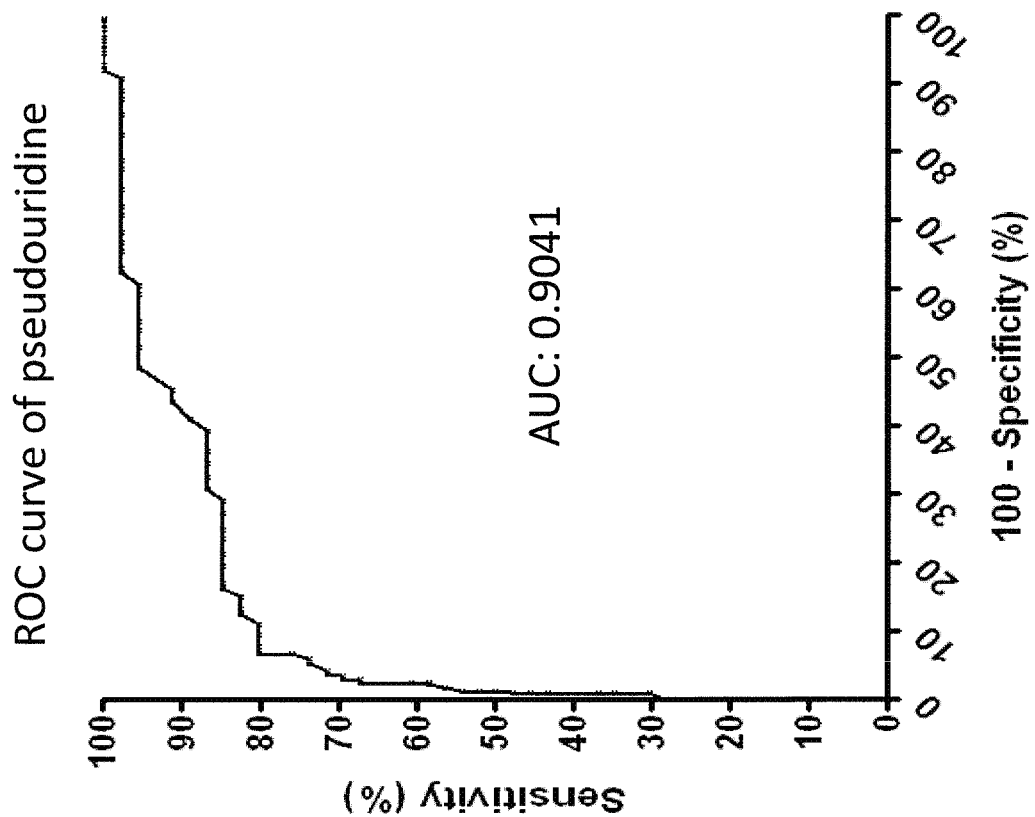
FIG. 5B is a graphical illustration of a ROC curve generated using the exemplary biomarker pseudouridine to distinguish CKD from Normal as described in Example 2.
Figure 5A:
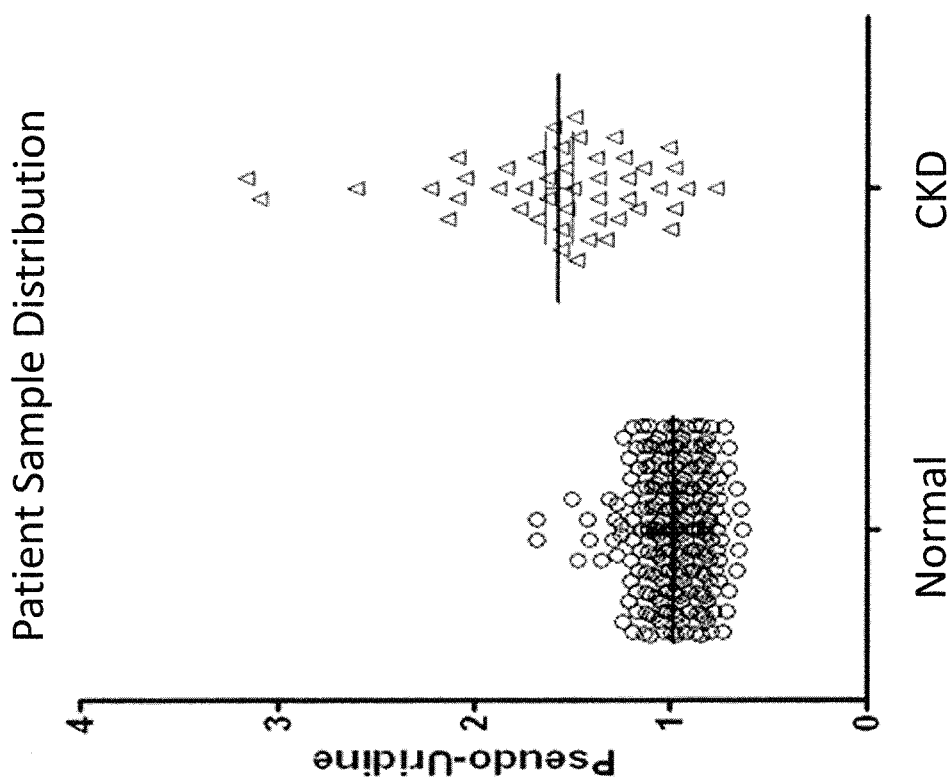
FIG. 5A is a graphical illustration of the distribution of patient serum samples based on the level of pseudouridine measured in the sample as described in Example 2.

The exemplary biomarker pseudouridine was also evaluated for diagnostic performance. FIG. 5A shows the distribution of patient samples based on the level of pseudouridine measured in the samples. The x-axis shows the diagnosis group (Normal or CKD), and the y-axis shows the level of pseudouridine. Next, the levels of pseudouridine were used in a mathematical model to determine the diagnostic performance of the biomarker. FIG. 5B shows the ROC curve for pseudouridine. The ROC curve has an AUC of 0.9041. Based on this ROC curve it was determined that by measuring the level of pseudouridine, CKD subjects were distinguished from Normal subjects with 80% sensitivity and 93% specificity.

Example 3: Diagnostic Performance of Panels of Biomarkers for Kidney Function Assessment In another example, mathematical models that provide an estimation of GFR were developed. These model GFR estimations were used to evaluate kidney function, and the performance of the estimations obtained using these models were compared to the eGFR calculated using the CKD-EPI equation ("CKD-EPI eGFR"). Five exemplary models were developed using combinations of the following biomarkers: pseudouridine, N-acetylthreonine, C-glycosyltryptophan, kynurenine, myo-inositol, creatinine. The exemplary biomarkers are also described in Example 1 as significant for distinguishing individuals with normal kidney function from those with CKD. These models are intended to be non-limiting and are presented to exemplify the invention.

The biomarkers pseudouridine, N-acetylthreonine, C-glycosyltryptophan, kynurenine, myo-inositol, and creatinine were measured in fasting serum samples collected from 258 diabetic individuals for whom the CKD-EPI equation to estimate GFR was used to evaluate kidney function. Patients with CKD-EPI eGFR values of 60 ml/min/1.73 m$^2$ or less were classified as having a "positive" diagnosis (i.e., compromised kidney function, CKD), and patients with eGFR values of greater than 60 ml/min/1.73 m$^2$ were classified as having a "negative" (i.e., normal kidney function). A total of 40 patients were classified as a positive diagnosis for CKD and/or compromised kidney function, and 218 patients were classified as a negative diagnosis and/or normal kidney function based on CKD-EPI eGFR results.

In the present example, five models were generated using multiple regression analysis: exemplary Model 1 comprises the biomarkers pseudouridine, glycosyltryptophan, N-acetylthreonine, and creatinine; exemplary Model 2 comprises the biomarkers pseudouridine, N-acetylthreonine, myo-inositol, and creatinine; exemplary Model 3 comprises the biomarkers N-acetylthreonine, myo-inositol, C-glycosyltryptophan, and creatinine; exemplary Model 4 comprises the biomarkers N-acetylthreonine, myo-inositol, kynurenine, and creatinine; and exemplary Model 5 comprises the biomarkers pseudouridine, C-glycosyltryptophan, N-acetylthreonine, and myo-inositol. Each model was evaluated for its diagnostic performance using Receiver Operating Characteristic (ROC) and by calculating the area under the curve (AUC).

Figure 6A:
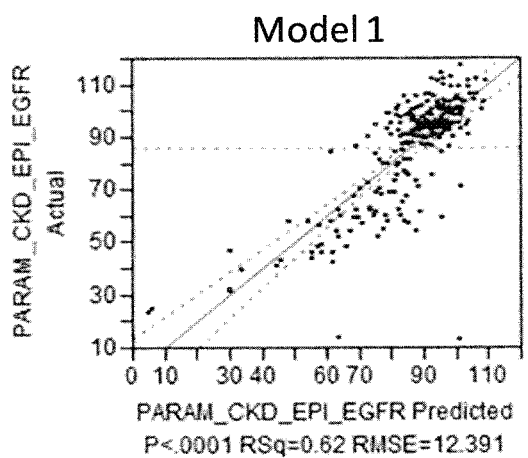
FIG. 6A is a graphical illustration of the correlation analysis of the estimated GFR calculated using Model 1 described in Example 3 with the eGFR calculated using the CKD-EPI equation.

For exemplary Model 1, the GFR values calculated using Model 1 were significantly correlated with the values calculated using the CKD-EPI eGFR; the adjusted R$^2$ was 0.614 with an overall p-value of less than 0.001. The diagnostic performance of Model 1 based on the calculated AUC was 0.932. The results of the correlation analysis for Model 1 are displayed graphically in FIG. 6A. The GFR calculated using Model 1 is plotted on the x-axis, and the CKD-EPI eGFR is plotted on the y-axis.

Figure 6B:
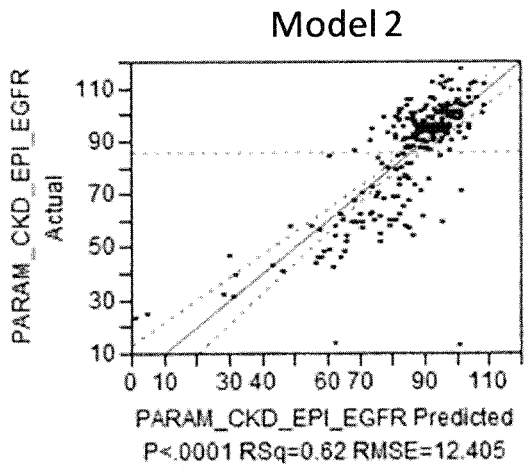
FIG. 6B is a graphical illustration of the correlation analysis of the estimated GFR calculated using Model 2 described in Example 3 with the eGFR calculated using the CKD-EPI equation.

For exemplary Model 2, the GFR values calculated using Model 2 were correlated with the values calculated using the CKD-EPI eGFR; the adjusted R$^2$ was 0.614 with an overall p-value of less than 0.0001. The diagnostic performance of Model 2 based on the calculated AUC was 0.932. The results of the correlation analysis for Model 2 are displayed graphically in FIG. 6B. The GFR calculated using Model 2 is plotted on the x-axis, and the CKD-EPI eGFR is plotted on the y-axis.

Figure 6C:
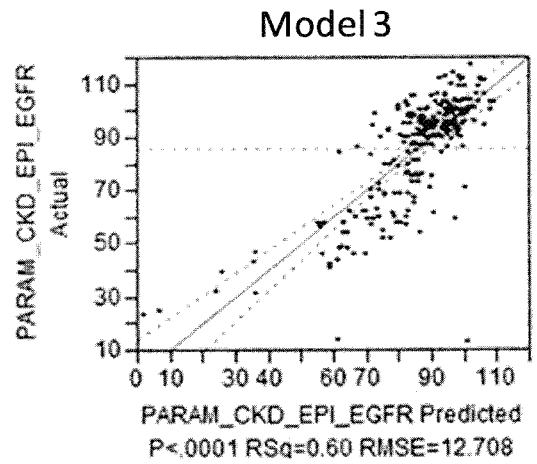
FIG. 6C is a graphical illustration of the correlation analysis of the estimated GFR calculated using Model 3 described in Example 3 with the eGFR calculated using the CKD-EPI equation.

For exemplary Model 3, the GFR values calculated using Model 3 were correlated with the values calculated using the CKD-EPI eGFR; the adjusted R$^2$ was 0.594 with an overall p-value of less than 0.0001. The diagnostic performance of Model 3 based on the calculated AUC was 0.931. The results of the correlation analysis for Model 3 are displayed graphically in FIG. 6C. The GFR calculated using Model 3 is plotted in the x-axis, and the CKD-EPI eGFR is plotted on the y-axis.

Figure 6D:
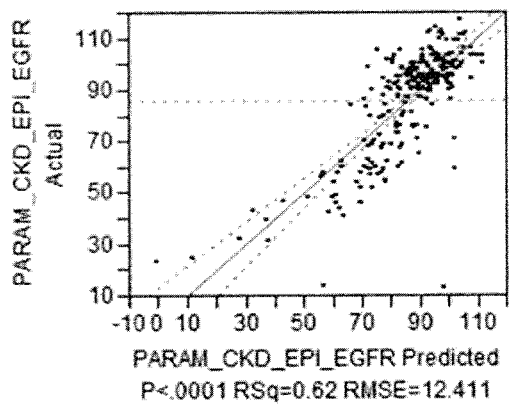
FIG. 6D is a graphical illustration of the correlation analysis of the estimated GFR calculated using Model 4 described in Example 3 with the eGFR calculated using the CKD-EPI equation.

For exemplary Model 4, the GFR values calculated using Model 4 were significantly correlated with the values calculated using the CKD-EPI eGFR; the adjusted R$^2$ was 0.613 with an overall p-value of less than 0.0001. The diagnostic performance of Model 4 based on the calculated AUC was 0.935. The results of the correlation analysis for Model 4 are displayed graphically in FIG. 6D. The GFR calculated using Model 4 is plotted on the x-axis, and the CKD-EPI eGFR is plotted on the y-axis.

Figure 6E:
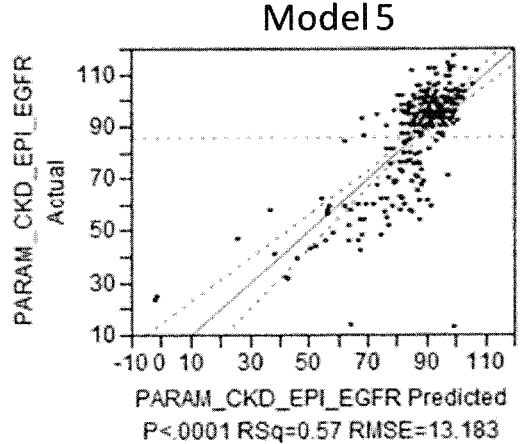
FIG. 6E is a graphical illustration of the correlation analysis of the estimated GFR calculated using Model 5 described in Example 3 with the eGFR calculated using the CKD-EPI equation.

For exemplary Model 5, the GFR values calculated using Model 5 were significantly correlated with the values calculated using the CKD-EPI eGFR; the adjusted R$^2$ was 0.563 with an overall p-value of less than 0.0001. The diagnostic performance of Model 5 based on the calculated AUC was 0.933. The results of the correlation analysis for Model 5 are displayed graphically in FIG. 6E. The GFR calculated using Model 5 is plotted on the x-axis, and the CKD-EPI eGFR is plotted on the y-axis.

Example 4: Biomarkers to Assess Kidney Function in Patients with Intermediate eGFR For patients with eGFR in an intermediate (G2-G3a) range with eGFR between 45 and 74 mL/min per 1.63 m$^2$ and/or intermediate urine albumin scores, the assessment of kidney function and diagnosis of CKD is uncertain; such patients would benefit from a more precisely estimated GFR such as a metabolite biomarker test. The integration of such a novel biomarker test into a kidney function assessment and treatment algorithm is illustrated in FIG. 1.

Biomarkers useful for evaluating kidney function and estimating GFR were identified by measuring the level of the biomarkers in serum samples and urine samples from diabetic individuals with eGFR values of 40-80.

Serum samples from 78 individuals for whom the MDRD eGFR and 69 individuals for whom the CKD-EPI eGFR values fell in this range were analyzed. The levels of the biomarkers were correlated with the MDRD eGFR and the CKD-EPI eGFR values. The results of the correlations are presented in Table 2. For each biomarker listed in Table 2 the biochemical name of the biomarker, the correlation value of the biomarker with CKD-EPI eGFR, the p-value of the correlation of the biomarker with CKD-EPI eGFR, the correlation value of the biomarker with MDRD eGFR, and the p-value of the correlation of the biomarker with MDRD eGFR are displayed.

TABLE 2

Serum biomarkers for assessing kidney function in patients with eGFR of 40-80

| Biomarker Name | CKD-EPI eGFR (Serum) | | MDRD eGFR (Serum) | |
| --- | --- | --- | --- | --- |
|  | Correlation | p-value | Correlation | p-value |
| pseudouridine | −0.6412 | 2.93E−09 | −0.6016 | 5.71E−09 |
| N-acetylthreonine | −0.5323 | 2.51E−06 | −0.5267 | 7.31E−07 |

TABLE 2-continued

Serum biomarkers for assessing kidney function in patients with eGFR of 40-80

| Biomarker Name | CKD-EPI eGFR (Serum) | | MDRD eGFR (Serum) | |
| --- | --- | --- | --- | --- |
| | Correlation | p-value | Correlation | p-value |
| C-glycosyltryptophan | −0.5614 | 5.20E−07 | −0.5153 | 1.39E−06 |
| X-11564 | −0.5685 | 3.47E−07 | −0.5206 | 1.03E−06 |
| N6-carbamoylthreonyladenosine | −0.5656 | 4.11E−07 | −0.5055 | 2.35E−06 |
| N4-acetylcytidine | −0.5451 | 1.28E−06 | −0.5687 | 5.58E−08 |
| N1-Methyl-2-pyridone-5-carboxamide | −0.524 | 3.83E−06 | −0.4698 | 1.43E−05 |
| urea | −0.5096 | 7.74E−06 | −0.5015 | 2.91E−06 |
| X-17299 | −0.501 | 1.16E−05 | −0.4468 | 4.11E−05 |
| N-acetylserine | −0.4931 | 1.67E−05 | −0.4459 | 4.29E−05 |
| 4-acetamidobutanoate | −0.4909 | 1.85E−05 | −0.4185 | 0.0001 |
| N-acetylalanine | −0.4803 | 2.96E−05 | −0.4185 | 0.0001 |
| creatinine | −0.4749 | 3.74E−05 | −0.4163 | 0.0002 |
| 5-methylthioadenosine (MTA) | −0.4518 | 9.74E−05 | −0.4319 | 7.86E−05 |
| glycerophosphorylcholine (GPC) | 0.4456 | 0.0001 | 0.4796 | 8.89E−06 |
| ribose | −0.4224 | 0.0003 | −0.4328 | 7.57E−05 |
| N1-methyladenosine | −0.4171 | 0.0004 | −0.3644 | 0.001 |
| phenylacetylglutamine | −0.4137 | 0.0004 | −0.3799 | 0.0006 |
| pro-hydroxy-pro | −0.4122 | 0.0004 | −0.415 | 0.0002 |
| propionylcarnitine | −0.4109 | 0.0005 | −0.4319 | 7.86E−05 |
| 2-methylbutyrylcarnitine (C5) | −0.4049 | 0.0006 | −0.3792 | 0.0006 |
| guanosine | −0.4043 | 0.0006 | −0.3719 | 0.0008 |
| succinylcarnitine | −0.3993 | 0.0007 | −0.3941 | 0.0004 |
| erythronate | −0.396 | 0.0008 | −0.3974 | 0.0003 |
| kynurenine | −0.3941 | 0.0008 | −0.31 | 0.0058 |
| N6-acetyllysine | −0.3908 | 0.0009 | −0.3466 | 0.0019 |
| choline | −0.3819 | 0.0012 | −0.2876 | 0.0107 |
| isobutyrylcarnitine | −0.381 | 0.0012 | −0.3827 | 0.0005 |
| tryptophan | 0.3738 | 0.0016 | 0.2994 | 0.0077 |
| myo-inositol | −0.3725 | 0.0016 | −0.3579 | 0.0013 |
| gamma-glutamylphenylalanine | −0.3716 | 0.0017 | −0.3651 | 0.001 |
| phenylcarnitine | −0.3711 | 0.0017 | −0.3876 | 0.0005 |
| palmitoyl sphingomyelin | 0.3695 | 0.0018 | 0.3686 | 0.0009 |
| salicyluric glucuronide | −0.3689 | 0.0018 | −0.3126 | 0.0053 |
| glutarylcarnitine (C5) | −0.367 | 0.0019 | −0.3391 | 0.0024 |
| S-adenosylhomocysteine (SAH) | −0.3619 | 0.0022 | −0.3438 | 0.0021 |
| furosemide | −0.3589 | 0.0025 | −0.3332 | 0.0029 |
| 1-methylhistidine | −0.3576 | 0.0026 | −0.3374 | 0.0025 |
| 2-hydroxyisobutyrate | −0.3555 | 0.0027 | −0.3352 | 0.0027 |
| p-cresol sulfate | −0.3531 | 0.0029 | −0.3042 | 0.0068 |
| 2-hydroxyhippurate (salicylurate) | −0.3472 | 0.0035 | −0.3223 | 0.004 |
| chiro-inositol | −0.3456 | 0.0036 | −0.3141 | 0.0051 |
| deoxycarnitine | −0.3419 | 0.004 | −0.287 | 0.0108 |
| O-methylcatechol sulfate | −0.3405 | 0.0042 | −0.3567 | 0.0013 |
| hydroxyisovaleroyl carnitine | −0.3384 | 0.0045 | −0.3166 | 0.0047 |
| N-delta-acetylornithine | −0.3322 | 0.0053 | −0.398 | 0.0003 |
| N2,N2-dimethylguanosine | −0.3264 | 0.0062 | −0.2851 | 0.0114 |
| xylonate | −0.3244 | 0.0065 | −0.2949 | 0.0088 |
| 3-methylglutarylcarnitine (C6) | −0.321 | 0.0072 | −0.2833 | 0.012 |
| gamma-glutamylvaline | −0.3172 | 0.0079 | −0.3666 | 0.001 |
| kynurenate | −0.3147 | 0.0084 | −0.2818 | 0.0124 |
| 1-pentadecanoylglycerophosphocholine | −0.3057 | 0.0106 | −0.3231 | 0.0039 |
| arabitol | −0.3052 | 0.0108 | −0.3268 | 0.0035 |
| stachydrine | −0.3045 | 0.011 | −0.2543 | 0.0247 |
| gamma-glutamylmethionine | −0.3004 | 0.0122 | −0.3254 | 0.0036 |
| cystine | −0.2994 | 0.0125 | −0.2351 | 0.0383 |
| fucose | −0.2906 | 0.0154 | −0.3022 | 0.0072 |
| 3-indoxyl sulfate | −0.282 | 0.0189 | −0.273 | 0.0156 |
| threitol | −0.2765 | 0.0214 | −0.2583 | 0.0224 |
| 1-linoleoylglycerol (1-monolinolein) | −0.2756 | 0.0219 | −0.2561 | 0.0236 |
| erythritol | −0.2748 | 0.0223 | −0.2691 | 0.0172 |
| N2,N5-diacetylornithine | −0.2673 | 0.0264 | −0.2862 | 0.0111 |
| N-formylmethionine | −0.264 | 0.0284 | −0.2501 | 0.0272 |
| N-acetylcarnosine | −0.2624 | 0.0294 | −0.184 | 0.1069 |
| 1-oleoylglycerol (1-monoolein) | −0.2607 | 0.0305 | −0.2573 | 0.0229 |
| pantothenate | −0.2584 | 0.032 | −0.2597 | 0.0217 |
| gamma-glutamylglutamine | −0.2546 | 0.0347 | −0.2871 | 0.0108 |
| arabonate | −0.2527 | 0.0362 | −0.2683 | 0.0176 |
| gamma-glutamylleucine | −0.2454 | 0.0421 | −0.282 | 0.0124 |
| tiglyl carnitine | −0.2428 | 0.0444 | −0.2551 | 0.0242 |
| cysteine | −0.2425 | 0.0447 | −0.2447 | 0.0308 |
| gamma-glutamyltyrosine | −0.2367 | 0.0502 | −0.2293 | 0.0434 |
| 2-aminophenol sulfate | −0.2326 | 0.0545 | −0.2402 | 0.0341 |

TABLE 2-continued

Serum biomarkers for assessing kidney function in patients with eGFR of 40-80

| Biomarker Name | CKD-EPI eGFR (Serum) | | MDRD eGFR (Serum) | |
|---|---|---|---|---|
| | Correlation | p-value | Correlation | p-value |
| 5-acetylamino-6-formylamino-3-methyluracil | −0.2297 | 0.0576 | −0.2185 | 0.0546 |
| ranitidine | −0.228 | 0.0595 | −0.213 | 0.0611 |
| salicylate | −0.2224 | 0.0662 | −0.1921 | 0.092 |
| hippurate | −0.221 | 0.068 | −0.2139 | 0.06 |
| catechol sulfate | −0.2164 | 0.0741 | −0.2564 | 0.0234 |
| N-acetylaspartate (NAA) | −0.2128 | 0.0791 | −0.1664 | 0.1455 |
| mannitol | −0.2122 | 0.08 | −0.1826 | 0.1096 |
| indolelactate | −0.2054 | 0.0905 | −0.1898 | 0.096 |
| N-acetyl-3-methylhistidine | −0.2051 | 0.091 | −0.188 | 0.0992 |
| gamma-glutamylisoleucine | −0.2039 | 0.0929 | −0.2494 | 0.0276 |
| phenol sulfate | −0.2002 | 0.0991 | −0.1723 | 0.1314 |
| gluconate | −0.1984 | 0.1022 | −0.2148 | 0.059 |
| trigonelline (N'-methylnicotinate) | −0.1846 | 0.1289 | −0.2241 | 0.0486 |
| HWESASLLR | −0.1778 | 0.1438 | −0.2589 | 0.0221 |
| N-acetylmethionine | −0.1731 | 0.155 | −0.206 | 0.0703 |
| acetylcarnitine | −0.1603 | 0.1883 | −0.2195 | 0.0535 |
| bilirubin (E,E) | 0.1558 | 0.2011 | 0.2033 | 0.0743 |
| theophylline | 0.1624 | 0.1825 | 0.2186 | 0.0545 |
| pregnen-diol disulfate | 0.1662 | 0.1722 | 0.2034 | 0.0741 |
| 4-androsten-3beta,17beta-diol disulfate 1 | 0.1689 | 0.1652 | 0.2002 | 0.0789 |
| oleamide | 0.1733 | 0.1544 | 0.2273 | 0.0453 |
| azelate (nonanedioate) | 0.1754 | 0.1494 | 0.2011 | 0.0775 |
| dehydroisoandrosterone sulfate (DHEA-S) | 0.1913 | 0.1153 | 0.2143 | 0.0596 |
| 1-palmitoylplasmenylethanolamine | 0.194 | 0.1101 | 0.214 | 0.0599 |
| 1-linoleoylglycerophosphoethanolamine | 0.2017 | 0.0964 | 0.1173 | 0.3063 |
| 3-methyl-2-oxovalerate | 0.2026 | 0.095 | 0.1736 | 0.1284 |
| 10-undecenoate (11:1n1) | 0.2033 | 0.0938 | 0.1418 | 0.2157 |
| 8-aminocaprylate | 0.2069 | 0.088 | −0.0025 | 0.9824 |
| 1-arachidonoylglycerophosphocholine | 0.2081 | 0.0861 | 0.1601 | 0.1615 |
| glutamine | 0.21 | 0.0833 | 0.2145 | 0.0594 |
| leucylphenylalanine | 0.2105 | 0.0825 | 0.1874 | 0.1004 |
| cholesterol | 0.2152 | 0.0758 | 0.1885 | 0.0983 |
| 3-ethylphenylsulfate | 0.2296 | 0.0577 | 0.1378 | 0.2289 |
| iminodiacetate (IDA) | 0.2313 | 0.0558 | 0.1771 | 0.1209 |
| cotinine N-oxide | 0.232 | 0.0551 | 0.136 | 0.2351 |
| glycerol | 0.233 | 0.0541 | 0.1679 | 0.1418 |
| 3-phosphoglycerate | 0.2362 | 0.0507 | 0.1999 | 0.0792 |
| campesterol | 0.2369 | 0.0501 | 0.1938 | 0.0891 |
| glycerol 2-phosphate | 0.2438 | 0.0435 | 0.2105 | 0.0644 |
| palmitate, methyl ester | 0.2446 | 0.0428 | 0.1984 | 0.0817 |
| octadecanedioate | 0.2446 | 0.0428 | 0.2531 | 0.0254 |
| 2-aminooctanoate | 0.2453 | 0.0422 | 0.2291 | 0.0436 |
| 1-linoleoylglycerophosphocholine | 0.2466 | 0.0411 | 0.1776 | 0.1199 |
| phosphate | 0.2481 | 0.0399 | 0.2361 | 0.0374 |
| pregnenolone sulfate | 0.2543 | 0.035 | 0.2531 | 0.0253 |
| glycerol 3-phosphate (G3P) | 0.2547 | 0.0347 | 0.2504 | 0.027 |
| 2-linoleoylglycerophosphocholine | 0.2611 | 0.0302 | 0.2151 | 0.0586 |
| glycerate | 0.2647 | 0.028 | 0.2837 | 0.0118 |
| sebacate (decanedioate) | 0.2733 | 0.0231 | 0.3051 | 0.0066 |
| isoleucylleucine | 0.2735 | 0.023 | 0.2405 | 0.0339 |
| EDTA | 0.2759 | 0.0218 | 0.2173 | 0.056 |
| beta-sitosterol | 0.2791 | 0.0202 | 0.2697 | 0.017 |
| pyrophosphate (PPi) | 0.2804 | 0.0196 | 0.2215 | 0.0513 |
| pregn steroid monosulfate | 0.283 | 0.0185 | 0.2907 | 0.0098 |
| eicosanodioate | 0.2836 | 0.0182 | 0.237 | 0.0367 |
| ethyl glucuronide | 0.2904 | 0.0155 | 0.2254 | 0.0472 |
| 2-hydroxyoctanoate | 0.2987 | 0.0127 | 0.2656 | 0.0187 |
| stearoyl sphingomyelin | 0.307 | 0.0103 | 0.3483 | 0.0018 |
| pyruvate | 0.3092 | 0.0097 | 0.2754 | 0.0147 |
| 8-hydroxyoctanoate | 0.3287 | 0.0058 | 0.3082 | 0.0061 |
| heptanoate (7:0) | 0.3308 | 0.0055 | 0.3516 | 0.0016 |
| adenosine 5'-monophosphate (AMP) | 0.3325 | 0.0053 | 0.3649 | 0.001 |
| caproate (6:0) | 0.3366 | 0.0047 | 0.3867 | 0.0005 |

Similarly, urine samples from 76 individuals for whom MDRD eGFR and 64 individuals for whom CKD-EPI eGFR values were in this range were analyzed. The measured levels of the biomarkers were correlated with MDRD eGFR and CKD-EPI eGFR values. The results of the correlations are presented in Table 3. For each biomarker, the biochemical name of the biomarker, the correlation value of the biomarker with CKD-EPI eGFR, the p-value of the correlation of the biomarker with CKD-EPI eGFR, the correlation value of the biomarker with MDRD eGFR, and the p-value of the correlation of the biomarker with MDRD eGFR is presented.

TABLE 3

Urine biomarkers to assess kidney function in patients with eGFR of 40-80

| Biochemical Name | CKD-EPI eGFR (Urine) | | MDRD eGFR (Urine) | |
| --- | --- | --- | --- | --- |
| | Correlation | p-value | Correlation | p-value |
| furosemide | −0.3835 | 0.0018 | −0.3193 | 0.0049 |
| myo-inositol | −0.3693 | 0.0027 | −0.3493 | 0.002 |
| chiro-inositol | −0.3255 | 0.0087 | −0.2936 | 0.01 |
| lactose | −0.2919 | 0.0192 | −0.269 | 0.0188 |
| quinolinate | −0.2729 | 0.0291 | −0.2023 | 0.0796 |
| homostachydrine | −0.2711 | 0.0302 | −0.1346 | 0.2464 |
| imidazole propionate | −0.2624 | 0.0362 | −0.1842 | 0.1111 |
| guanidinosuccinate | −0.2498 | 0.0465 | −0.2972 | 0.0091 |
| 2-oxo-1-pyrrolidinepropionate | −0.2451 | 0.0509 | −0.257 | 0.025 |
| N-acetylphenylalanine | −0.2384 | 0.0578 | −0.2052 | 0.0754 |
| N1-Methyl-2-pyridone-5-carboxamide | −0.2339 | 0.0629 | −0.1986 | 0.0855 |
| stachydrine | −0.2335 | 0.0633 | −0.1122 | 0.3345 |
| N4-acetylcytidine | −0.2327 | 0.0642 | −0.1837 | 0.1122 |
| N-acetyltryptophan | −0.2305 | 0.0669 | −0.2546 | 0.0264 |
| ofloxacin | −0.2297 | 0.0679 | −0.2365 | 0.0397 |
| 5-oxoproline | −0.2254 | 0.0733 | −0.0409 | 0.7258 |
| 1,3,7-trimethylurate | −0.2203 | 0.0802 | −0.106 | 0.362 |
| isosorbide | −0.218 | 0.0835 | −0.1914 | 0.0976 |
| hydroquinone sulfate | −0.2177 | 0.084 | −0.2127 | 0.0651 |
| 5-methyltetrahydrofolate (5MeTHF) | −0.2145 | 0.0888 | −0.2145 | 0.0628 |
| hydantoin-5-propionic acid | −0.2116 | 0.0933 | −0.2143 | 0.063 |
| mannitol | −0.2107 | 0.0947 | −0.1993 | 0.0844 |
| nicotinate | −0.2039 | 0.1061 | −0.1992 | 0.0845 |
| abscisate | −0.2028 | 0.108 | −0.1704 | 0.1412 |
| pipecolate | −0.2026 | 0.1083 | −0.2191 | 0.0572 |
| N-acetyltyrosine | −0.1898 | 0.133 | −0.1349 | 0.2452 |
| N-(2-furoyl)glycine | −0.1871 | 0.1388 | −0.1657 | 0.1525 |
| 1,7-dimethylurate | −0.187 | 0.139 | −0.1136 | 0.3284 |
| kynurenine | −0.1794 | 0.1561 | −0.1828 | 0.114 |
| alpha-CEHC glucuronide | −0.1764 | 0.1632 | −0.1362 | 0.2406 |
| guanidine | −0.173 | 0.1716 | −0.2664 | 0.02 |
| O-methylcatechol sulfate | −0.1677 | 0.1853 | −0.1881 | 0.1037 |
| orotidine | −0.1676 | 0.1856 | −0.1075 | 0.3552 |
| 3-methoxytyrosine | −0.1674 | 0.1862 | −0.1364 | 0.2401 |
| neopterin | −0.1673 | 0.1863 | −0.1842 | 0.1112 |
| alanylleucine | −0.1573 | 0.2144 | −0.1742 | 0.1323 |
| 3-dehydrocarnitine | −0.1541 | 0.224 | −0.1272 | 0.2736 |
| phenylcarnitine | −0.1494 | 0.2388 | −0.1504 | 0.1947 |
| caffeine | −0.1464 | 0.2485 | −0.1437 | 0.2155 |
| orotate | −0.1425 | 0.2614 | −0.0994 | 0.3932 |
| arginylisoleucine | −0.141 | 0.2663 | −0.1034 | 0.3743 |
| N-acetyl-aspartyl-glutamate (NAAG) | 0.1428 | 0.2605 | 0.0904 | 0.4373 |
| hypoxanthine | 0.1436 | 0.2576 | 0.0962 | 0.4084 |
| 3-methylcytidine | 0.1437 | 0.2574 | 0.1196 | 0.3033 |
| N-acetylglycine | 0.1461 | 0.2494 | 0.0563 | 0.6292 |
| mandelate | 0.1473 | 0.2454 | 0.0434 | 0.7094 |
| androsterone sulfate | 0.1484 | 0.2419 | 0.1093 | 0.3472 |
| 2,3-dihydroxyisovalerate | 0.1489 | 0.2404 | 0.0527 | 0.651 |
| taurine | 0.149 | 0.24 | 0.0706 | 0.5442 |
| dehydroisoandrosterone sulfate (DHEA-S) | 0.1494 | 0.2387 | 0.1481 | 0.2018 |
| N-acetylthreonine | 0.15 | 0.2369 | 0.0387 | 0.7401 |
| itaconate (methylenesuccinate) | 0.1503 | 0.2358 | 0.0151 | 0.8971 |
| homoveratric acid | 0.1522 | 0.2299 | 0.1318 | 0.2564 |
| verapamil | 0.1522 | 0.2299 | 0.2047 | 0.0761 |
| 1-methylhistidine | 0.1544 | 0.2233 | 0.0946 | 0.4161 |
| 3-hydroxybutyrate (BHBA) | 0.1557 | 0.2192 | 0.0518 | 0.6568 |
| alanine | 0.1557 | 0.2191 | 0.098 | 0.3999 |
| pantothenate | 0.1563 | 0.2173 | 0.1216 | 0.2953 |
| methyl indole-3-acetate | 0.1571 | 0.2151 | 0.0894 | 0.4422 |
| N2-acetyllysine | 0.1625 | 0.1996 | 0.286 | 0.0123 |
| 4-acetaminophen sulfate | 0.1634 | 0.197 | 0.1829 | 0.1138 |
| cis-aconitate | 0.1638 | 0.196 | 0.0496 | 0.6706 |
| 5-hydroxyhexanoate | 0.1639 | 0.1957 | 0.0866 | 0.4569 |
| allo-threonine | 0.1646 | 0.1936 | 0.0796 | 0.4945 |

TABLE 3-continued

Urine biomarkers to assess kidney function in patients with eGFR of 40-80

| Biochemical Name | CKD-EPI eGFR (Urine) | | MDRD eGFR (Urine) | |
|---|---|---|---|---|
| | Correlation | p-value | Correlation | p-value |
| 2-hydroxybutyrate (AHB) | 0.1647 | 0.1933 | 0.062 | 0.5947 |
| homocitrate | 0.1649 | 0.1928 | 0.106 | 0.362 |
| acisoga | 0.1651 | 0.1924 | 0.141 | 0.2243 |
| arabinose | 0.1667 | 0.188 | 0.0469 | 0.6874 |
| lactate | 0.1682 | 0.184 | 0.0733 | 0.5292 |
| gentisate | 0.1701 | 0.1791 | 0.0824 | 0.4792 |
| N-acetylhistidine | 0.1707 | 0.1775 | 0.1738 | 0.1332 |
| gamma-glutamylvaline | 0.1732 | 0.1712 | 0.1248 | 0.2828 |
| beta-hydroxyisovalerate | 0.1747 | 0.1674 | 0.0821 | 0.481 |
| N-acetylproline | 0.1757 | 0.1649 | 0.0402 | 0.7303 |
| 7-methylguanine | 0.1761 | 0.164 | 0.1013 | 0.3839 |
| arabitol | 0.177 | 0.1618 | 0.0695 | 0.551 |
| cortisol | 0.1777 | 0.1601 | 0.1648 | 0.1547 |
| 4-methyl-2-oxopentanoate | 0.1778 | 0.1598 | 0.0846 | 0.4673 |
| putrescine | 0.1788 | 0.1575 | 0.0585 | 0.6156 |
| 2-isopropylmalate | 0.1789 | 0.1572 | 0.0691 | 0.5533 |
| trans-urocanate | 0.1803 | 0.154 | 0.1788 | 0.1222 |
| tyrosine | 0.1803 | 0.154 | 0.1657 | 0.1526 |
| andro steroid monosulfate 2 | 0.1818 | 0.1505 | 0.1449 | 0.2117 |
| sulforaphane | 0.182 | 0.15 | 0.1276 | 0.272 |
| glycine | 0.1827 | 0.1484 | 0.2002 | 0.0829 |
| 4-androsten-3beta,17beta-diol disulfate 1 | 0.1897 | 0.1332 | 0.1766 | 0.1271 |
| 7-ketodeoxycholate | 0.1899 | 0.1328 | 0.2549 | 0.0263 |
| 3-ureidopropionate | 0.1935 | 0.1255 | 0.1318 | 0.2563 |
| 3-methylglutaconate | 0.1936 | 0.1252 | 0.0987 | 0.3963 |
| cotinine | 0.1968 | 0.119 | 0.0939 | 0.4197 |
| tartarate | 0.1973 | 0.1182 | 0.0788 | 0.4984 |
| ethanolamine | 0.2005 | 0.1122 | 0.2327 | 0.0431 |
| N1-methylguanosine | 0.2015 | 0.1103 | 0.2281 | 0.0475 |
| succinimide | 0.2036 | 0.1066 | 0.0815 | 0.4839 |
| malate | 0.2083 | 0.0986 | 0.0894 | 0.4423 |
| 3-hydroxyglutarate | 0.209 | 0.0974 | 0.1233 | 0.2884 |
| 3-(3-hydroxyphenyl)propionate | 0.2093 | 0.097 | 0.142 | 0.221 |
| 2-piperidinone | 0.213 | 0.0911 | 0.1119 | 0.3359 |
| 3-hydroxyisobutyrate | 0.214 | 0.0895 | 0.1118 | 0.3365 |
| ibuprofen acyl glucuronide | 0.2147 | 0.0885 | 0.1785 | 0.1229 |
| pregnanediol-3-glucuronide | 0.2163 | 0.086 | 0.0902 | 0.4384 |
| lysine | 0.2171 | 0.0848 | 0.2017 | 0.0806 |
| adipate | 0.2196 | 0.0813 | 0.1126 | 0.3326 |
| 3-methylglutarate | 0.2197 | 0.0811 | 0.1089 | 0.3489 |
| tetrahydrocortisone | 0.2207 | 0.0797 | 0.1809 | 0.1178 |
| prolylglycine | 0.2215 | 0.0786 | 0.102 | 0.3808 |
| o-cresol sulfate | 0.223 | 0.0765 | 0.1157 | 0.3196 |
| 5alpha-pregnan-3beta,20alpha-diol disulfate | 0.224 | 0.0751 | 0.1073 | 0.3564 |
| histidine | 0.2267 | 0.0716 | 0.1705 | 0.1408 |
| 3-ethylphenylsulfate | 0.2278 | 0.0703 | 0.1169 | 0.3145 |
| gamma-glutamylisoleucine | 0.2295 | 0.0681 | 0.1393 | 0.23 |
| andro steroid monosulfate 1 | 0.2305 | 0.0669 | 0.1617 | 0.163 |
| citramalate | 0.2393 | 0.0568 | 0.0874 | 0.4526 |
| 2-hydroxyglutarate | 0.2467 | 0.0494 | 0.1025 | 0.3782 |
| 3-hydroxy-3-methylglutarate | 0.2474 | 0.0488 | 0.1151 | 0.322 |
| 3-methoxy-4-hydroxyphenylglycol | 0.2487 | 0.0475 | 0.1276 | 0.2719 |
| guanidinoacetate | 0.2487 | 0.0475 | 0.3448 | 0.0023 |
| ethyl glucuronide | 0.2502 | 0.0461 | 0.1545 | 0.1826 |
| 3-hydroxypropanoate | 0.2509 | 0.0455 | 0.1692 | 0.1439 |
| N-acetylisoleucine | 0.2511 | 0.0453 | 0.1146 | 0.3241 |
| pregnen-diol disulfate | 0.2515 | 0.045 | 0.1932 | 0.0944 |
| thymol sulfate | 0.2516 | 0.0449 | 0.2185 | 0.0579 |
| citrate | 0.252 | 0.0445 | 0.1569 | 0.1759 |
| 3-dehydrocholate | 0.2537 | 0.0431 | 0.221 | 0.0551 |
| sorbitol | 0.2545 | 0.0424 | 0.1737 | 0.1334 |
| argininosuccinate | 0.2563 | 0.0409 | 0.1956 | 0.0905 |
| glucosamine | 0.2604 | 0.0377 | 0.1624 | 0.1611 |
| N6-methyladenosine | 0.2666 | 0.0332 | 0.1903 | 0.0996 |
| S-methylcysteine | 0.2688 | 0.0317 | 0.1516 | 0.1911 |
| 2-aminoadipate | 0.2725 | 0.0294 | 0.2413 | 0.0357 |
| 5,6-dihydrouracil | 0.2759 | 0.0273 | 0.2008 | 0.082 |
| N-acetylaspartate (NAA) | 0.2832 | 0.0234 | 0.1778 | 0.1245 |
| xylitol | 0.285 | 0.0225 | 0.1951 | 0.0913 |
| N1-methyladenosine | 0.2859 | 0.022 | 0.2608 | 0.0229 |
| N6-acetyllysine | 0.2981 | 0.0167 | 0.2376 | 0.0388 |

TABLE 3-continued

Urine biomarkers to assess kidney function in patients with eGFR of 40-80

| Biochemical Name | CKD-EPI eGFR (Urine) | | MDRD eGFR (Urine) | |
|---|---|---|---|---|
| | Correlation | p-value | Correlation | p-value |
| uracil | 0.305 | 0.0142 | 0.3646 | 0.0012 |
| 4-androsten-3beta,17beta-diol disulfate 2 | 0.3071 | 0.0136 | 0.2664 | 0.02 |
| 21-hydroxypregnenolone disulfate | 0.318 | 0.0104 | 0.219 | 0.0573 |
| tryptophan | 0.32 | 0.01 | 0.2654 | 0.0205 |
| 3-methyl-2-oxovalerate | 0.3278 | 0.0082 | 0.2353 | 0.0408 |
| N2-methylguanosine | 0.3307 | 0.0076 | 0.3335 | 0.0032 |
| ribitol | 0.3366 | 0.0065 | 0.2194 | 0.0568 |
| N-acetyl-beta-alanine | 0.338 | 0.0063 | 0.2264 | 0.0493 |
| ribulose | 0.3382 | 0.0063 | 0.2708 | 0.018 |
| glycolate (hydroxyacetate) | 0.3563 | 0.0039 | 0.3646 | 0.0012 |
| gamma-aminobutyrate (GABA) | 0.3611 | 0.0034 | 0.2828 | 0.0133 |
| thymine | 0.3706 | 0.0026 | 0.3172 | 0.0052 |

In another example, using the patient serum samples described in Example 1, samples with eGFR CKD-EPI values of 40-80 were further classified as having High or Low eGFR values. Patient samples with eGFR values of 40-60 were classified as having Low eGFR; patient samples with eGFR values of 61-80 were classified as having High eGFR. A total of 41 patients were classified as having Low eGFR, and 42 patients were classified as having High eGFR at the time of sample collection.

The levels of metabolites were measured and the results were analyzed using t-tests. Biomarkers for kidney function in patients with intermediate eGFR measurements (e.g., CKD-EPI eGFR calculations of 40-80) were analyzed by comparing High (eGFR calculation of 61-80) vs. Low (eGFR calculation of 40-60) samples. As listed in Table 4, the analysis resulted in the identification of biomarkers that were differentially present between patient serum samples with High eGFR and those with Low eGFR.

Table 4 includes, for each biomarker, the biochemical name of the biomarker, the fold change of the biomarker in subjects with High eGFR compared to subjects with Low eGFR (High/Low, is the ratio of the mean level of the biomarker in samples from patients with CKD-EPI eGFR of 61-80 compared to the mean level in samples from patients with CKD-EPI eGFR of 40-60), and the p-value and q-value determined in the statistical analysis of the data concerning the biomarkers. Table 4 also lists the following: the internal identifier for the biomarker compound (CompID); the identifier for the biomarker compound in the Kyoto Encyclopedia of Genes and Genomes (KEGG), if available; and the identifier for the biomarker compound in the Human Metabolome Database (HMDB), if available.

TABLE 4

Serum biomarkers to assess kidney function in patients with eGFR of 40-80

| Biochemical Name | HIGH/LOW | | | | | |
|---|---|---|---|---|---|---|
| | Fold Change | p-value | q-value | Comp ID | KEGG | HMDB |
| pseudouridine | 0.75 | p < 0.0001 | 0.0009 | 33442 | C02067 | HMDB00767 |
| N-acetylthreonine | 0.79 | p < 0.0001 | 0.0097 | 33939 | C01118 | |
| C-glycosyltryptophan | 0.74 | p < 0.0001 | 0.0021 | 32675 | | |
| N6-carbamoylthreonyladenosine | 0.73 | p < 0.0001 | 0.0021 | 35157 | | HMDB41623 |
| N4-acetylcytidine | 0.72 | p < 0.0001 | 0.0097 | 35130 | | HMDB05923 |
| erythronate | 0.78 | 0.0001 | 0.0097 | 33477 | | HMDB00613 |
| X-11564 | 0.76 | 0.0001 | 0.0097 | 32881 | | |
| N1-methyladenosine | 0.86 | 0.0002 | 0.0131 | 15650 | C02494 | HMDB03331 |
| 3-methylglutarylcarnitine (C6) | 0.68 | 0.0004 | 0.02 | 37060 | | HMDB00552 |
| 5-methylthioadenosine (MTA) | 0.62 | 0.0004 | 0.02 | 1419 | C00170 | HMDB01173 |
| glycerophosphorylcholine (GPC) | 1.45 | 0.0007 | 0.0288 | 15990 | C00670 | HMDB00086 |
| ADpSGEGDFXAEGGGVR | 2.54 | 0.0008 | 0.0288 | 33801 | | |
| tryptophan | 1.14 | 0.0009 | 0.0314 | 54 | C00078 | HMDB00929 |
| N-formylmethionine | 0.81 | 0.0013 | 0.0422 | 2829 | C03145 | HMDB01015 |
| 2-hydroxyisobutyrate | 0.46 | 0.0015 | 0.0451 | 22030 | | HMDB00729 |
| fucose | 0.72 | 0.0017 | 0.0461 | 15821 | C01018 | HMDB00174 |
| succinylcarnitine | 0.75 | 0.0021 | 0.0553 | 37058 | | |
| N-acetylserine | 0.78 | 0.0027 | 0.0636 | 37076 | | HMDB02931 |
| N-acetylalanine | 0.88 | 0.0028 | 0.0636 | 1585 | C02847 | HMDB00766 |
| 4-acetamidobutanoate | 0.81 | 0.0028 | 0.0636 | 1558 | C02946 | HMDB03681 |
| 1-docosapentaenoylglycerophosphocholine (22:5n3) | 1.38 | 0.0032 | 0.0688 | 37231 | | |
| myo-inositol | 0.75 | 0.0034 | 0.0722 | 19934 | C00137 | HMDB00211 |
| gluconate | 0.73 | 0.0046 | 0.0886 | 587 | C00257 | HMDB00625 |

TABLE 4-continued

Serum biomarkers to assess kidney function in patients with eGFR of 40-80

| Biochemical Name | HIGH/LOW Fold Change | p-value | q-value | Comp ID | KEGG | HMDB |
|---|---|---|---|---|---|---|
| 1-linoleoylglycerol (1-monolinolein) | 0.62 | 0.005 | 0.0907 | 27447 | | |
| ribitol | 0.83 | 0.0058 | 0.0961 | 15772 | C00474 | HMDB00508 |
| N1-Methyl-2-pyridone-5-carboxamide | 0.78 | 0.0061 | 0.0983 | 40469 | C05842 | HMDB04193 |
| arabitol | 0.78 | 0.0071 | 0.1064 | 38075 | C01904 | HMDB01851 |
| octadecanedioate | 1.31 | 0.009 | 0.1233 | 36754 | | HMDB00782 |
| eicosapentaenoate (EPA; 20:5n3) | 1.58 | 0.0093 | 0.1247 | 18467 | C06428 | HMDB01999 |
| cortisol | 0.86 | 0.0095 | 0.1247 | 1712 | C00735 | HMDB00063 |
| erythritol | 0.76 | 0.0119 | 0.1461 | 20699 | C00503 | HMDB02994 |
| furosemide | 0.47 | 0.0124 | 0.1461 | 43009 | D00331 | HMDB01933 |
| caffeine | 1.54 | 0.0126 | 0.1461 | 569 | C07481 | HMDB01847 |
| 1-docosahexaenoylglycerophosphocholine (22:6n3) | 1.36 | 0.0127 | 0.1461 | 33822 | | |
| ergothioneine | 0.48 | 0.0127 | 0.1461 | 37459 | C05570 | HMDB03045 |
| saccharin | 3.34 | 0.0132 | 0.1481 | 21151 | D01085 | HMDB29723 |
| guanosine | 0.78 | 0.0137 | 0.1481 | 1573 | C00387 | HMDB00133 |
| ethyl glucuronide | 2.51 | 0.0141 | 0.1487 | 39603 | | |
| N2,N2-dimethylguanosine | 0.85 | 0.0155 | 0.1521 | 35137 | | HMDB04824 |
| 10-undecenoate (11:1n1) | 1.37 | 0.0157 | 0.1521 | 32497 | | |
| 1-methylxanthine | 1.45 | 0.0177 | 0.1618 | 34389 | C16358 | HMDB10738 |
| theophylline | 1.66 | 0.0181 | 0.1632 | 18394 | C07130 | HMDB01889 |
| pregn steroid monosulfate | 1.61 | 0.0187 | 0.1632 | 32619 | | |
| N2,N5-diacetylornithine | 0.71 | 0.0191 | 0.1632 | 43591 | | |
| paraxanthine | 1.43 | 0.0191 | 0.1632 | 18254 | C13747 | HMDB01860 |
| pro-hydroxy-pro | 0.75 | 0.0224 | 0.1747 | 35127 | | HMDB06695 |
| 8-aminocaprylate | 2.17 | 0.0224 | 0.1747 | 21161 | | |
| pantothenate | 0.82 | 0.0227 | 0.1748 | 1508 | C00864 | HMDB00210 |
| azelate (nonanedioate) | 2.99 | 0.0232 | 0.1764 | 18362 | C08261 | HMDB00784 |
| DSGEGDFXAEGGGVR | 2.72 | 0.0239 | 0.1797 | 31548 | | |
| 1-arachidonoylglycerophosphocholine (20:4n6) | 1.28 | 0.0261 | 0.1934 | 33228 | C05208 | |
| acisoga | 0.78 | 0.0284 | 0.2034 | 43258 | | |
| creatinine | 0.89 | 0.0309 | 0.2144 | 513 | C00791 | HMDB00562 |
| X-17299 | 0.87 | 0.0314 | 0.2144 | 40097 | | |
| 2-arachidonoylglycerophosphocholine | 1.32 | 0.0317 | 0.2144 | 35256 | | |
| isoleucylleucine | 1.28 | 0.032 | 0.2144 | 36760 | | |
| ADSGEGDFXAEGGGVR | 1.84 | 0.0341 | 0.2229 | 33084 | | |
| 1-linoleoylglycerophosphocholine (18:2n6) | 1.21 | 0.0342 | 0.2229 | 34419 | C04100 | |
| stearoyl sphingomyelin | 1.15 | 0.0346 | 0.2229 | 19503 | C00550 | HMDB01348 |
| indoleacetylglutamine | 0.86 | 0.0366 | 0.2288 | 42087 | | HMDB13240 |
| 5-oxoproline | 1.16 | 0.0371 | 0.2295 | 1494 | C01879 | HMDB00267 |
| dimethylarginine (SDMA + ADMA) | 0.65 | 0.0377 | 0.2311 | 36808 | C03626 | HMDB01539 |
| ribose | 0.71 | 0.0389 | 0.2314 | 12080 | C00121 | HMDB00283 |
| urea | 0.87 | 0.039 | 0.2314 | 1670 | C00086 | HMDB00294 |
| docosahexaenoate (DHA; 22:6n3) | 1.21 | 0.0393 | 0.2314 | 19323 | C06429 | HMDB02183 |
| threitol | 0.7 | 0.0415 | 0.2401 | 35854 | C16884 | HMDB04136 |
| propionylcarnitine | 0.84 | 0.0443 | 0.2534 | 32452 | C03017 | HMDB00824 |
| 1,3-dihydroxyacetone | 0.6 | 0.0458 | 0.2534 | 35963 | C00184 | HMDB01882 |
| 2-methylbutyrylcarnitine (C5) | 0.77 | 0.0464 | 0.2547 | 35431 | | HMDB00378 |
| 2-aminobutyrate | 1.19 | 0.0487 | 0.2624 | 32309 | C02261 | HMDB00650 |
| xylonate | 0.71 | 0.0497 | 0.2633 | 35638 | C05411 | HMDB60256 |

While the invention has been described in detail and with reference to specific embodiments thereof, it will be apparent to one skilled in the art that various changes and modifications can be made without departing from the spirit and scope of the invention.

What is claimed is:

1. A method of determining and treating kidney function impairment in a subject, the method comprising:

a) extracting small molecules from a biological sample obtained from the subject to produce an analytical sample;

b) performing or having performed an assay on the analytical sample to determine the level(s) of one or more biomarkers, wherein the one or more biomarkers are selected from the group consisting of the following biomarkers: N-acetylthreonine, N-acetylalanine, arabitol, N-acetylserine, erythronate, 4-acetamidobutanoate, N6-carbamoylthreonyladenosine, N-acetylcarnosine, arabonate, xylonate, N-formylmethionine, O-methylcatechol sulfate, N-acetylmethionine, N2,N5-diacetylornithine, ribose, pyroglutamine, 5-methylthioadenosine (MTA), 1-methylurate, pro-hydroxy-pro, N-acetyl-3-methylhistidine, 2,3-dihydroxyisovalerate, trigonelline (N'-methylnicotinate), X-11564, and X-17299;

c) determining kidney function impairment in the subject by comparing the level(s) of the one or more biomarkers in the sample to kidney function reference levels of the one or more biomarkers in order to determine impaired kidney function in the subject; and d) administering an effective treatment to the subject having impaired kidney function, wherein effective treatment comprises one or more of weight loss, healthy diet, smoking cessation, high blood pressure treatment, performing or having performed dialysis, or performing or having performed a kidney transplant.

2. The method of claim 1, further comprising
performing or having performed an assay on the analytical sample to determine the level(s) of one or more additional biomarkers selected from the group consisting of the following biomarkers: trans-4-hydroxyproline, myo-inositol, kynurenine, tryptophan, 3-methylhistidine, erythritol, urea, 3-methylglutarylcarnitine (C6), S-adenosylhomocysteine (SAH), N1-methyladenosine, N2,N2-dimethylguanosine, p-cresol sulfate, succinylcarnitine, 2-methylbutyrylcarnitine (C5), N4-acetylcytidine, N1-Methyl-2-pyridone-5-carboxamide, 1-methylhistidine, tiglyl carnitine, isobutyrylcarnitine, indolelactate, glutarylcarnitine (C5), choline, hydroxyisovaleroyl carnitine, scyllo-inositol, quinate, salicyluric glucuronide, 2-mannopyranosyl tryptophan (2-MPT), creatinine, phenylacetyl-L-glutamine, 3-indoxylsulfate, pseudouridine, N6-acetyllysine, threitol and 2-hydroxyhippurate (salicylurate).

3. The method of claim 1, further comprising using the determined levels of the one or more biomarkers in a mathematical model to calculate an estimated glomerular filtration rate (GFR) to determine kidney function impairment.

4. The method of claim 3, wherein the sample is analyzed using one or more techniques selected from the group consisting of mass spectrometry, ELISA, and antibody linkage.

5. The method of claim 1, wherein the sample is obtained from a subject that has no symptoms of impaired kidney function.

6. The method of claim 1, wherein the subject has been previously diagnosed with hypertension and/or diabetes.

7. The method of claim 1, wherein the subject has symptoms of impaired kidney function.

8. The method of claim 1, wherein the subject is one for whom kidney function assessment using conventional methods is difficult.

9. The method of claim 8, wherein the subject is selected from the group consisting of the following: obese, very lean, vegetarian, chronically ill, and elderly.

10. The method of claim 1, further comprising performing additional analysis related to the one or more additional markers and methods and/or measures comprising BUN, serum creatinine (SCr), urine albumin measurements, family history of chronic kidney disease (CKD), β-2 microglobulin, or β-TRACE, and combining results of the additional analysis with the assessment results from the initial assessment steps.

11. A method of preventing impaired kidney function in a subject being considered for treatment with a composition wherein the composition is selected from the group consisting of a chemotherapeutic agent, an antibiotic, and a contrast imaging agent, wherein the composition may have a toxic effect on the kidneys, the method comprising:

a) extracting small molecules from a biological sample obtained from the subject to produce an analytical sample;

b) performing, or having performed, an assay on the analytical sample to determine the level(s) of one or more biomarkers, wherein the one or more biomarkers are selected from the group consisting of the following biomarkers: N-acetylthreonine, N-acetylalanine, arabitol, N-acetylserine, erythronate, 4-acetamidobutanoate, N6-carbamoylthreonyladenosine, N-acetylcarnosine, arabonate, xylonate, N-formylmethionine, O-methylcatechol sulfate, N-acetylmethionine, N2,N5-diacetylornithine, ribose, pyroglutamine, 5-methylthioadenosine (MTA), 1-methylurate, pro-hydroxy-pro, N-acetyl-3-methylhistidine, 2,3-dihydroxyisovalerate, trigonelline (N'-methylnicotinate), X-11564, and X-17299; and c) performing or having performed an assay on the analytical sample to determine the level(s) of one or more additional biomarkers selected from the group consisting of the following biomarkers: trans-4-hydroxyproline, myo-inositol, kynurenine, tryptophan, 3-methylhistidine, erythritol, urea, 3-methylglutarylcarnitine (C6), S-adenosylhomocysteine (SAH), N1-methyladenosine, N2,N2-dimethylguanosine, p-cresol sulfate, succinylcarnitine, 2-methylbutyrylcarnitine (C5), N4-acetylcytidine, N1-Methyl-2-pyridone-5-carboxamide, 1-methylhistidine, tiglyl carnitine, isobutyrylcarnitine, indolelactate, glutarylcarnitine (C5), choline, hydroxyisovaleroyl carnitine, scyllo-inositol, quinate, salicyluric glucuronide, 2-mannopyranosyl tryptophan (2-MPT), creatinine, phenylacetyl-L-glutamine, 3-indoxylsulfate, pseudouridine, N6-acetyllysine, threitol and 2-hydroxyhippurate (salicylurate); and d) using the determined levels of the one or more biomarkers and, optionally, the one or more additional biomarkers, in a mathematical model to calculate an estimated glomerular filtration rate (GFR);

e) using the estimated GFR to determine kidney function in the subject, and
  i. administering the chemotherapeutic agent, antibiotic, and/or contrast imaging agent to the subject having normal kidney function,
  ii. decreasing the dosage of the chemotherapeutic agent, antibiotic, and/or contrast imaging agent or selecting a different chemotherapeutic agent, antibiotic, and/or contrast imaging agent to administer to the subject having moderately impaired kidney function, or
  iii. decreasing the dosage of the chemotherapeutic agent, antibiotic, and/or contrast imaging agent, selecting a different chemotherapeutic agent, antibiotic, and/or contrast imaging agent, or selecting a different treatment intervention or diagnostic test for the subject having severely impaired kidney function.

12. A method of monitoring kidney function to prevent impaired kidney function in a subject wherein the subject has been treated with a composition that may impair kidney function, wherein the composition is administered to a subject to treat a disease or condition and wherein risk of kidney damage from treatment with the composition for a subject having impaired kidney function is higher than for a subject not having impaired kidney function, the method comprising:
  a) extracting small molecules from a biological sample obtained from a subject treated with a composition that may have a toxic effect on the kidneys;
  b) performing or having performed an assay on a first biological sample from the subject to determine the level(s) of one or more biomarkers for kidney function, where the one or more biomarkers are selected from the group consisting of the following biomarkers: N-acetylthreonine, N-acetylalanine, arabitol, N-acetylserine, erythronate, 4-acetamidobutanoate, N6-carbamoylthreonyladenosine, N-acetylcarnosine, arabonate, xylonate, N-formylmethionine, O-methylcatechol sulfate, N-acetylmethionine, N2,N5-diacetylornithine, ribose, pyroglutamine, 5-methylthioadenosine (MTA), 1-methylurate, pro-hydroxy-pro, N-acetyl-3-methylhistidine, 2,3-dihydroxyisovalerate, trigonelline (N'-methylnicotinate), X-11564, and X-17299;
  c) performing or having performed the assay on a second biological sample from the subject to determine the level(s) of the one or more biomarkers for kidney function, wherein the second sample is obtained from the subject at a second time point; and
  d) monitoring kidney function in the subject by comparing the level(s) of one or more biomarkers in the second sample to the level(s) of the one or more biomarkers in (a) the first sample and/or (b) kidney function reference levels of the one or more biomarkers, and
    i. continuing to administer the composition to the subject having kidney function that remains in a normal range,
    ii. decreasing the dosage of the composition or selecting a different composition for treating the subject having kidney function that is moderately impaired, or
    iii. discontinuing treatment with the composition and selecting a different composition or treatment regimen; or continuing treatment by administering a decreased dosage of the composition to the subject having kidney function that is severely impaired.

13. The method of claim 12, further comprising
performing or having performed an assay on the first biological sample and the second biological sample from the subject to determine the level(s) of one or more additional biomarkers selected from the group consisting of the following biomarkers: trans-4-hydroxyproline, myo-inositol, kynurenine, tryptophan, 3-methylhistidine, erythritol, urea, 3-methylglutarylcarnitine (C6), S-adenosylhomocysteine (SAH), N1-methyladenosine, N2,N2-dimethylguanosine, p-cresol sulfate, succinylcarnitine, 2-methylbutyrylcarnitine (C5), N4-acetylcytidine, N1-Methyl-2-pyridone-5-carboxamide, 1-methylhistidine, tiglyl carnitine, isobutyrylcarnitine, indolelactate, glutarylcarnitine (C5), choline, hydroxyisovaleroyl carnitine, scyllo-inositol, quinate, salicyluric glucuronide, 2-mannopyranosyl tryptophan (2-MPT), creatinine, phenylacetyl-L-glutamine, 3-indoxylsulfate, pseudouridine, N6-acetyllysine, threitol and 2-hydroxyhippurate (salicylurate).

14. The method of claim 12, further comprising using the determined levels of the one or more biomarkers in a mathematical model to calculate an estimated glomerular filtration rate (GFR); and using the estimated GFR to monitor kidney function.

15. A method to determine or aid in the determination of kidney function in a subject who is a potential kidney donor, the method comprising:
  a) extracting small molecules from a biological sample obtained from the subject to produce an analytical sample;
  b) performing or having performed an assay on the analytical sample from the subject to determine the level(s) of one or more biomarkers, wherein the one or more biomarkers are selected from the group consisting of the following biomarkers: N-acetylthreonine, N-acetylalanine, arabitol, N-acetylserine, erythronate, 4-acetamidobutanoate, N6-carbamoylthreonyladenosine, N-acetylcarnosine, arabonate, xylonate, N-formylmethionine, O-methylcatechol sulfate, N-acetylmethionine, N2,N5-diacetylornithine, ribose, pyroglutamine, 5-methylthioadenosine (MTA), 1-methylurate, pro-hydroxy-pro, N-acetyl-3-methylhistidine, 2,3-dihydroxyisovalerate, trigonelline (N'-methylnicotinate), X-11564, and X-17299;
  c) using the determined level(s) of the one or more biomarkers in a mathematical model to calculate an estimated glomerular filtration rate (GFR);
  d) using the estimated GFR to determine kidney function of the potential donor, and
  e) performing or having performed a kidney transplant using a kidney of the potential donor having normal kidney function.

16. The method of claim 12, further comprising
performing additional analysis related to one or more additional markers and methods and/or measures comprising BUN, serum creatinine, urine albumin measurements, β-2 microglobulin, β-TRACE, or family history of chronic kidney disease (CKD), wherein the one or more additional biomarkers are selected from the group consisting of trans-4-hydroxyproline, myo-inositol, kynurenine, tryptophan, 3-methylhistidine, erythritol, urea, 3-methylglutarylcarnitine (C6), S-adenosylhomocysteine (SAH), N1-methyladenosine, N2,N2-dimethylguanosine, p-cresol sulfate, succinylcarnitine, 2-methylbutyrylcarnitine (C5), N4-acetylcytidine, N1-Methyl-2-pyridone-5-carboxamide, 1-methylhistidine, tiglyl carnitine, isobutyrylcarnitine, indolelactate, glutarylcarnitine (C5), choline, hydroxyisovaleroyl carnitine, scyllo-inositol, quinate, salicyluric glucuronide, 2-mannopyranosyl tryptophan (2-MPT), creatinine, phenylacetyl-L-glutamine, 3-indoxylsulfate, pseudouridine, N6-acetyllysine, threitol and 2-hydroxyhippurate (salicylurate), and
combining results of the additional analysis with the assessment results from the initial assessment steps.

17. The method of claim 12, wherein the composition is selected from the group consisting of a chemotherapeutic agent, a contrast imaging agent and an antibiotic.

* * * * *